US012691183B2

(12) United States Patent
Shukla et al.

(10) Patent No.: US 12,691,183 B2
(45) Date of Patent: Jul. 28, 2026

(54) METHODS OF MAKING AND USING NANOPARTICLES FOR TREATMENT OF BACTERIAL BIOFILM

(71) Applicant: Brown University, Providence, RI (US)

(72) Inventors: Anita Shukla, East Greenwich, RI (US); Yingying Wang, Providence, RI (US)

(73) Assignee: Brown University, Providence, RI (US)

( * ) Notice: Subject to any disclaimer, the term of this patent is extended or adjusted under 35 U.S.C. 154(b) by 533 days.

(21) Appl. No.: 18/175,610

(22) Filed: Feb. 28, 2023

(65) Prior Publication Data

US 2023/0277683 A1 Sep. 7, 2023

Related U.S. Application Data

(60) Provisional application No. 63/317,201, filed on Mar. 7, 2022.

(51) Int. Cl.
| | |
|---|---|
| *A61K 47/69* | (2017.01) |
| *A61K 31/65* | (2006.01) |
| *A61P 31/04* | (2006.01) |
| *B82Y 5/00* | (2011.01) |

(52) U.S. Cl.
CPC .......... *A61K 47/6939* (2017.08); *A61K 31/65* (2013.01); *A61P 31/04* (2018.01); *B82Y 5/00* (2013.01)

(58) Field of Classification Search
None
See application file for complete search history.

(56) References Cited

U.S. PATENT DOCUMENTS

| | | | |
|---|---|---|---|
| 4,107,288 A | 8/1978 | Oppenheim et al. | |
| 10,426,842 B2 | 10/2019 | Kannan et al. | |
| 2007/0207182 A1* | 9/2007 | Weber ..................... | A61L 29/12 607/2 |
| 2012/0093894 A1* | 4/2012 | Yu .......................... | A61P 27/02 514/456 |
| 2013/0338233 A1* | 12/2013 | Cegelski ............... | A01N 35/02 514/679 |

FOREIGN PATENT DOCUMENTS

| | | |
|---|---|---|
| CN | 102010513 B | 1/2013 |
| KR | 101528197 B1 | 6/2015 |
| WO | 2018190755 A1 | 10/2018 |

OTHER PUBLICATIONS

Tatsiana G. Shutava et al. "Layer-by-Layer-Coated Gelatin Nanoparticles as a Vehicle for Delivery of Natural Polyphenols." ACS Nano, vol. 3, No. 7, 2009, pp. 1877-1885 and 4 pages of supplemental information. (Year: 2009).*

Shutava, et al. Layer-by-layer-coated gelatin nanoparticles as a vehicle for delivery of natural polyphenols. ACS Nano, vol. 3. No. 7, 1877-1885, 2009.

(Continued)

*Primary Examiner* — Isaac Shomer

(74) *Attorney, Agent, or Firm* — Banner & Witcoff, Ltd.

(57) ABSTRACT

A method of making and using nanoparticles that target bacterial biofilm are provided.

7 Claims, 9 Drawing Sheets
(2 of 9 Drawing Sheet(s) Filed in Color)

(56)     References Cited

OTHER PUBLICATIONS

Carvalho et al. Functionalized photosensitive gelatin nanoparticles for drug delivery application. Journal of Biomaterials Science, Polymer Edition 2019, vol. 30, No. 7, 508-525.

Lin, et al. Bacteria-Responsive Biomimetic Selenium Nanosystem for Multidrug-Resistant Bacterial Infection Detection and Inhibition. ACS Nano 2019, 13, 13965-13984.

Li, et al. Core-shell supramolecular gelatin nanoparticles for adaptive and "on-demand" antibiotic delivery. ACS Nano, vol. 8, No. 5, 4975-4983, 2014.

Su et al. Preparation and Characterization of Erythrocyte Membrane-Camouflaged Berberine Hydrochloride-Loaded Gelatin Nanoparticles. Pharmaceutics 2019, 11, 93.

Kirar et al. Porphyrin Functionalized Gelatin Nanoparticle-Based Biodegradable Phototheranostics: Potential Tools for Antimicrobial Photodynamic Therapy. ACS Appl. Bio Mater. 2019, 2, 4202-4212.

Balthasar et al. Preparation and characterisation of antibody modified gelatin nanoparticles as drug carrier system for uptake in lymphocytes. Biomaterials 26 (2005) 2723-2732.

Tian, et al. Blood-brain barrier transport of Tat peptide and polyethylene glycol decorated gelatin-siloxane nanoparticle. Materials Letters. 68 (2012) 94-96.

* cited by examiner

METHODS OF MAKING AND USING NANOPARTICLES FOR TREATMENT OF BACTERIAL BIOFILM

RELATED APPLICATIONS

This application claims the benefit of U.S. provisional application No. 63/317,201 and filed Mar. 7, 2022 which is hereby incorporated by reference in its entirety.

STATEMENT OF GOVERNMENT INTERESTS

This invention was made with government support under N00014-17-2120 awarded by the Office of Naval Research. The government has certain rights in the invention.

FIELD

The present invention relates in general to the design and use of nanoparticles to penetrate bacterial biofilms and release a payload, such as an antimicrobial agent.

BACKGROUND

Biofilm-associated bacterial infections are considered as one of the greatest threats to health worldwide. It is estimated that around 17 million new biofilm-associated infections arise and lead to up to 550,000 deaths annually in the United States alone. See R. J. Worthington, J. J. Richards and C. Melander, *Org. Biomol. Chem.,* 2012, 10, 7457-7474. Bacterial biofilms are complex, three-dimensional bacterial communities that are embedded in a self-produced matrix of extracellular polymeric substances (EPS), which includes proteins, polysaccharides, extracellular DNA, and lipids. See R. Joseph, A. Naugolny, M. Feldman, I. M. Herzog, M. Fridman and Y. Cohen, *Journal of the American Chemical Society,* 2016, 138, 754-757. Biofilms are involved in various conditions including dental caries, urinary tract infections, burn wound infections, diabetic foot ulcers. See Y. Liu, L. Shi, L. Su, H. C. van der Mei, P. C. Jutte, Y. Ren and H. J. Busscher, *Chem. Soc. Rev.,* 2019, 48, 428-446.

Currently, the most commonly used method for treatment of biofilm-related infections is oral or intravenous administration of United States Food and Drug Administration (FDA) approved antibiotics. See C. Deusenbery, Y. Wang and A. Shukla, *ACS Infectious Diseases,* 2021, 7, 695-720. However, the recalcitrance of biofilms toward antibiotics impairs the therapeutic effect of this traditional therapy. See D. Davies, *Nature Reviews Drug Discovery,* 2003, 2, 114-122, and D. Lebeaux, J.-M. Ghigo and C. Beloin, *Microbiol Mol Biol Rev.,* 2014, 78, 510-543. In fact, high antibiotic doses (up to 10-1000 times greater than concentrations effective against planktonic bacteria) and prolonged treatment times are usually required for the treatment of biofilm-associated bacterial infections, which can exacerbate toxicity and resistance. See T.-F. Mah, B. Pitts, B. Pellock, G. C. Walker, P. S. Stewart and G. A. O'Toole, *Nature,* 2003, 426, 306-310 and P. Bowler, C. Murphy, R. Wolcott, *Antimicrobial Resistance and Infection Control,* 2020, 9, 162.

With recent advances in nanotechnology, nanomaterials have shown promise as new antimicrobials and delivery systems to combat biofilm-associated bacterial infection. See S. Fulaz, S. Vitale, L. Quinn and E. Casey, *Trends in Microbiology,* 2019, 27, 915-926. Numerous nanomaterials have been reported as promising antibiotic alternatives such as metal-based nanoparticles (NPs) (e.g. silver nanoparticles (see Y. Dong, H. Zhu, Y. Shen, W. Zhang and L. Zhang,

*PLoS One,* 2019, 14, e0222322 and X. Dai, Q. Guo, Y. Zhao, P. Zhang, T. Zhang, X. Zhang and C. Li, *ACS Applied Materials & Interfaces,* 2016, 8, 25798-25807), gold nanoparticles (see X. Yang, J. Yang, L. Wang, B. Ran, Y. Jia, L. Zhang, G. Yang, H. Shao and X. Jiang, *ACS Nano,* 2017, 11, 5737-5745) and palladium nanoparticles (see G. Fang, W. Li, X. Shen, J. M. Perez-Aguilar, Y Chong, X. Gao, Z. Chai, C. Chen, C. Ge and R. Zhou, *Nature Communications,* 2018, 9, 129), cationic polymeric NPs (see A. Gupta, R. F. Landis, C.-H. Li, M. Schnurr, R. Das, Y-W. Lee, M. Yazdani, Y Liu, A. Kozlova and V. M. Rotello, *Journal of the American Chemical Society,* 2018, 140, 12137-12143; X. K. Liu, Lihong, H. Wang, P. K. J. Tan, W. Fan, S. S. Venkatraman, L. Li and Y.-Y. Yang, *Nature Nanotechnology,* 2009, 4, 457-463; and A. Ivanova, K. Ivanova, J. Hoyo, T. Heinze, S. Sanchez-Gomez and T. Tzanov, *ACS Applied Materials & Interfaces,* 2018, 10, 3314-3323), and quantum dots (see C. M. Courtney, S. M. Goodman, J. A. McDaniel, N. E. Madinger, A. Chatterjee and P. Nagpal, *Nature Materials,* 2016, 15, 529-534). However, methods and materials are needed for the treatment of bacterial infections which can overcome the resistance provided by the bacterial biofilm.

SUMMARY

Aspects of the present disclosure are directed to nanoparticles and methods of using such nanoparticles to treat bacterial biofilm and the bacteria within, which contributes to bacterial resistance. According to one aspect, the nanoparticles penetrate the bacterial biofilm. After the nanoparticle has penetrated the bacterial biofilm, the nanoparticle releases a payload agent. The payload agent may be an antimicrobial, which is toxic to the bacteria within the bacterial biofilm. According to one aspect, the bacteria die, and therefore cease to produce the bacterial biofilm. As a result, the bacterial biofilm is destroyed or otherwise eradicated. The payload agent may also be a drug directed specifically to the biofilm, such as an antibiofilm peptide. The payload agent may also be a detectable agent, such as a fluorescent dye, which can be used to detect the presence of the biofilm, thereby providing a diagnostic agent and a method of diagnosis of a bacterial infection.

The present disclosure describes methods of treating an individual in need thereof for a bacterial infection. The nanoparticles described herein are administered to an individual and penetrate a bacterial biofilm within the individual. The nanoparticles release an antimicrobial within the bacterial biofilm thereby treating the individual for the bacterial infection.

According to one aspect, the nanoparticle includes a core. The core is or includes the payload agent, such as an antibiotic, a bactericide, or other antimicrobial agent. The nanoparticle includes a layer or coating on or otherwise surrounding the core. The layer or coating is responsive to a first condition or environment of the biofilm which exposes the core which then releases the payload agent. According to one aspect, the core is responsive to a second condition or environment of the biofilm to release the payload agent. It is to be understood that the term nanoparticle includes a particle having a core and one or more layers. According to one aspect, the nanoparticle includes a core and one or more, two or more or a plurality of layers. An antimicrobial agent may be present in the core or in one or more layers or both.

According to one aspect, the nanoparticles described herein are effective to inhibit or otherwise prevent biofilm formation. According to one aspect, the nanoparticles described herein are effective to inhibit or prevent growth of existing biofilms. According to one aspect, the nanoparticles described herein are effective to reduce the presence of existing biofilms or otherwise destroy or eradicate existing biofilms.

Further features and advantages of certain embodiments of the present invention will become more fully apparent in the following description of embodiments and drawings thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present embodiments will be more fully understood from the following detailed description of illustrative embodiments taken in conjunction with the accompanying drawings in which:

FIG. 2(a) Hydrodynamic size distribution and ζ-potential of GNPs determined by DLS. Results are shown as mean±standard deviation. Statistical significance (*p<0.05, *p<0.001 and **p<0.0001) between groups is indicated using two-way ANOVA with Tukey's post hoc analysis; n=3. FIG. 2(b) SEM images of NPs. Scale bar: 500 nm. SEM images are representative of at least three imaged NPs.

FIG. 3(a) Spectral scan of Doxy aqueous solutions with different concentrations. FIG. 3(b) Linear regions of plots of absorbance at 340 nm as a function of Doxy concentrations. Data are shown as mean±standard deviation (n=3).

4

Figures 6A, 6B:
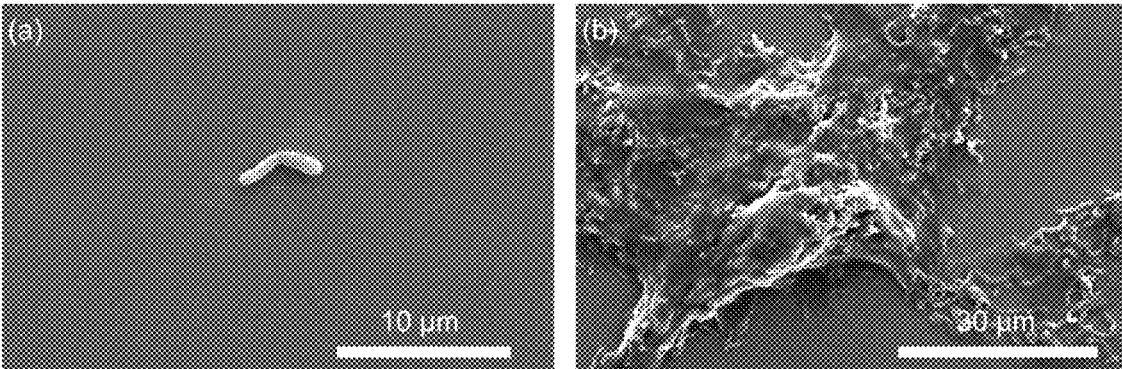

FIGS. 6(a)-(b) SEM images of FIG. 6(a) planktonic V. vulnificus and FIG. 6(b) V. vulnificus biofilm on silicon wafer. SEM images are representatives of at least three repeats.

Figures 7A, 7B, 7C, 7D:
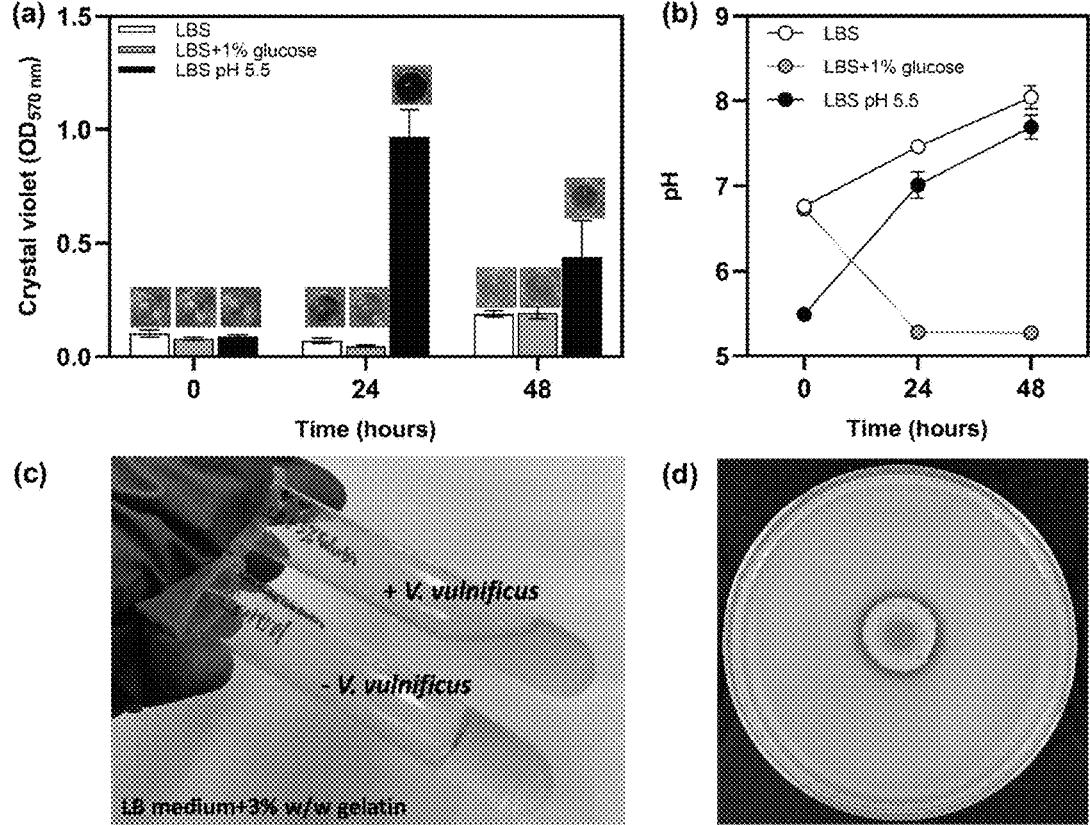

FIGS. 7(a)-(d) Characterization of the formation and microenvironment of V. vulnificus biofilm. FIG. 7(a) crystal violet assay was used to assess the formation of V. vulnificus in different conditions, including LBS, LBS with 1% w/v glucose and LBS at pH 5.5. OD570 was read to indicate biofilm biomass. All solutions were measured directly except samples from 24 h. All three conditions at 24 h were dilute 10-fold before reading OD570. Image above each column was taken after extracted crystal violet. FIG. 7(b) pH change of V. vulnificus biofilm which were formed in different growth media. FIG. 7(c) Gelatin hydrolysis test of V. vulnificus. FIG. 7(d) A plate method for the detection of hyaluronidase. Data are shown as mean±standard deviation (n=3). Gelatin hydrolysis test and hyaluronidase test were done at least three times.

Figure 8:
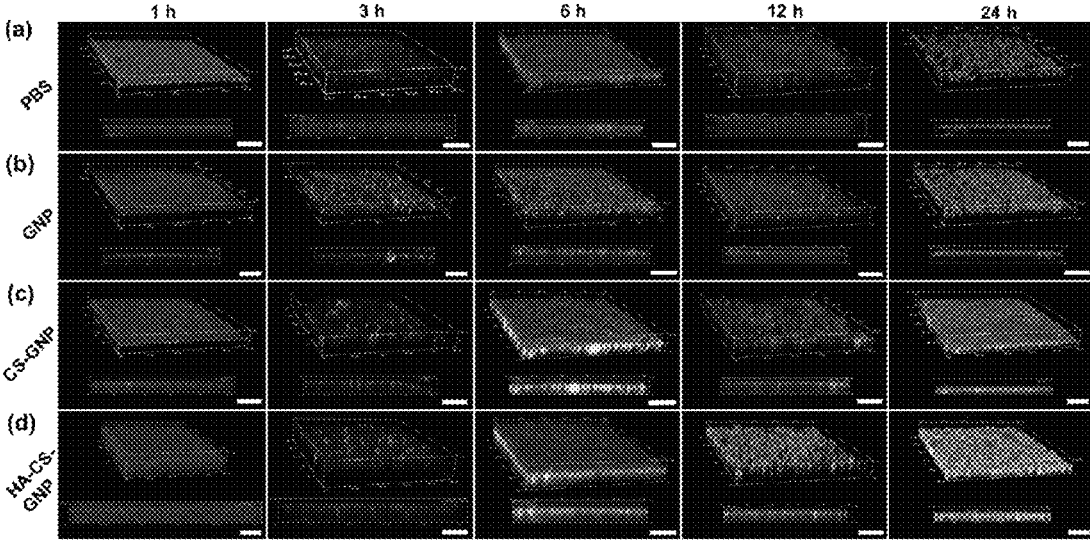

FIG. 8 In vitro penetration assay toward 48 h matured V. vulnificus biofilms. Confocal images of V. vulnificus biofilms after treating with 1×PBS, GNPs (1 mg/mL), CS-GNPs (1 mg/mL), and HA-CS-GNPs (1 mg/mL) in different durations (1 h, 3 h, 6 h, 12 h and 24 h). Red represents biofilm, and green indicates NPs. Scale bar: 100 μm. CLSM images are representative of at least three imaged biofilms.

Figures 9A, 9B:
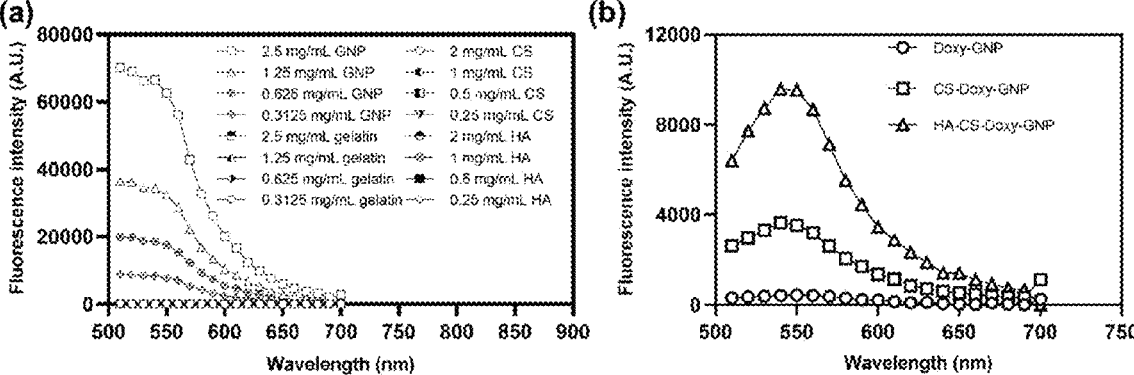

FIGS. 9(a)-(b) Fluorescence spectra of FIG. 9(a) blank GNPs, gelatin, CS, HA with different concentrations and FIG. 9(b) 100 μg/mL Doxy loaded NPs.

Figures 10A, 10B:
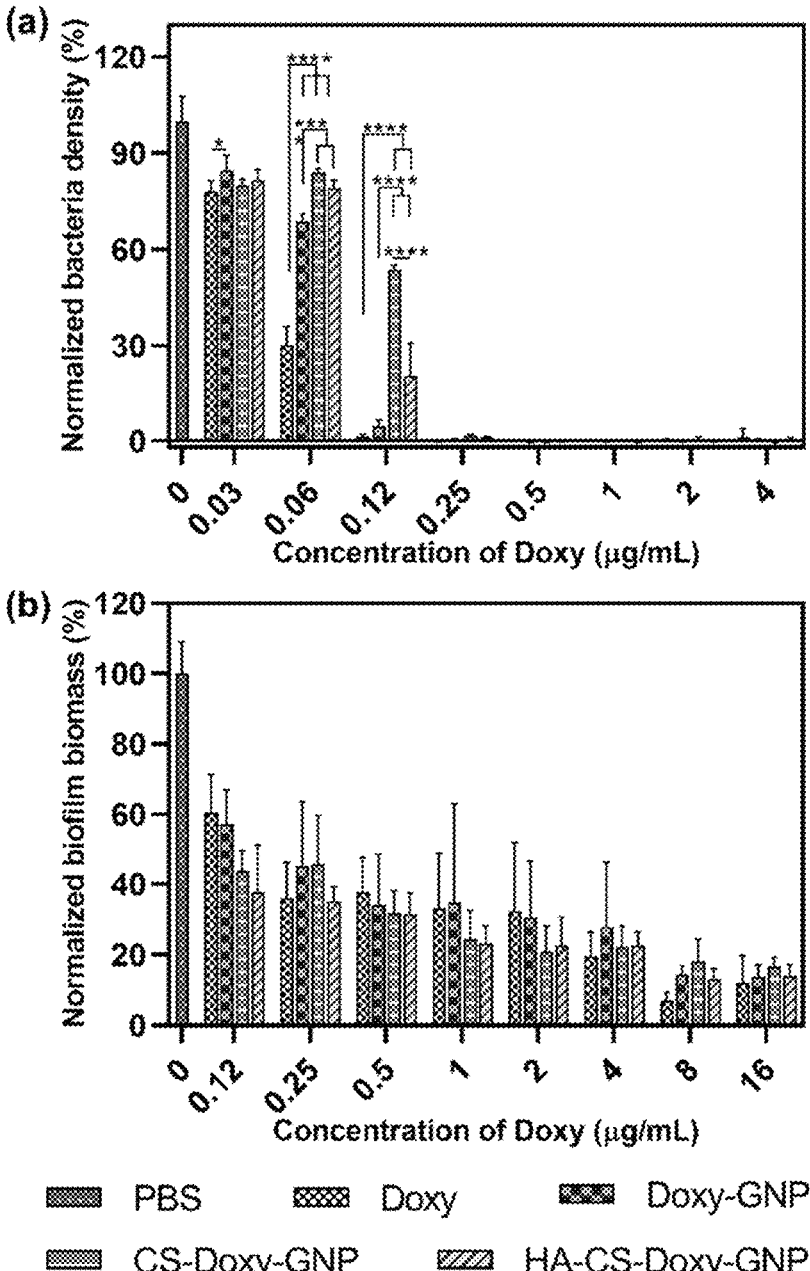

FIGS. 10(a)-(b) FIG. 10(a) Antibacterial efficacy and FIG. 10(b) the inhibition efficacy against biofilms of free Doxy and Doxy loaded NPs with different concentrations. Results are shown as mean±standard deviation. Statistical significance (*p<0.05, ****p<0.0001) between groups is indicated using two-way ANOVA with Tukey's post hoc analysis, n=3.

Figures 11A, 11B, 11C:
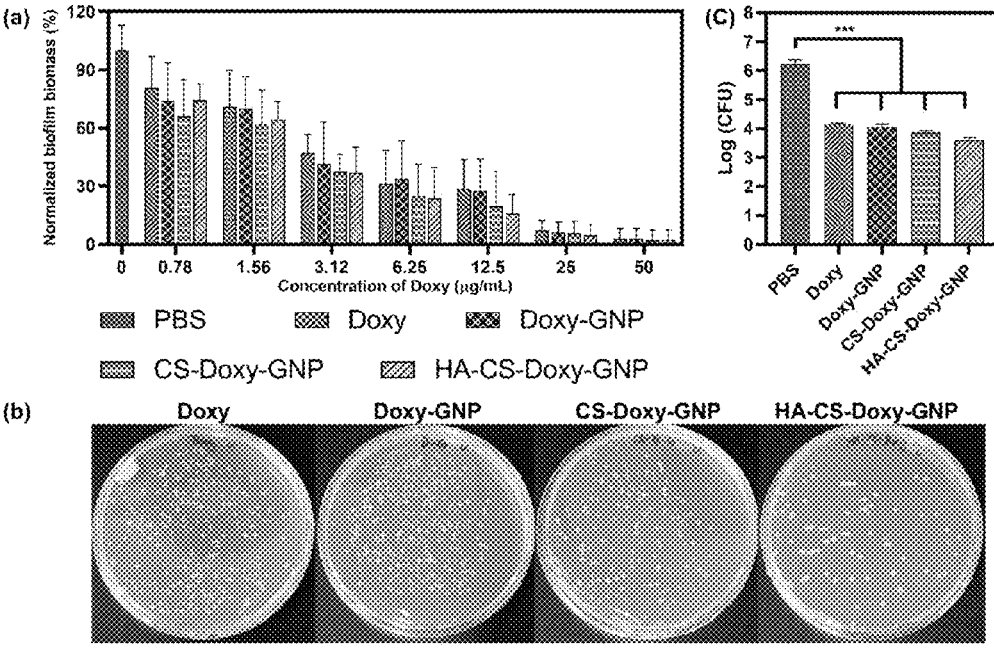

FIGS. 11(a)-(c) Eradication effect of NPs toward V. vulnificus biofilm. FIG. 11(a) The normalized biofilm biomass after treating with Doxy, Doxy-GNPs, CS-Doxy-GNPs and HA-CS-Doxy-GNPs with various concentrations. FIG. 11(b) Photographs of bacterial colonies formed and FIG. 11(c) CFU number of V. vulnificus biofilm after treated with PBS, 50 μg/mL Doxy and Doxy loaded NPs (50 μg/mL Doxy) for 24 h. Results are shown as mean±standard deviation. Statistical significance ***p<0.001) between groups is indicated using one-way ANOVA with Tukey's post hoc analysis, n=3. The photographs of bacterial colonies on agar are representatives of at least three repeats.

Figures 12A, 12B:
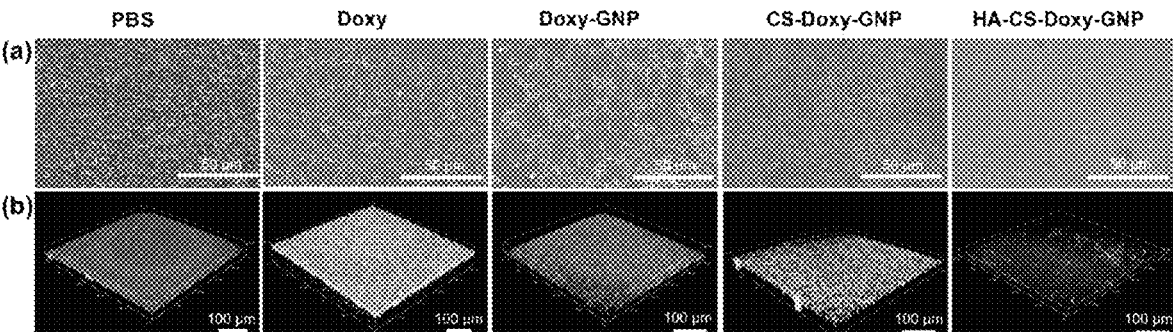

FIGS. 12(a)-(b) Eradication effect of NPs toward V. vulnificus biofilm. FIG. 12(a) SEM images, FIG. 12(b) LIVE/DEAD staining of V. vulnificus biofilm after treated with PBS, 50 μg/mL Doxy and Doxy loaded NPs (50 μg/mL Doxy) for 24 h. Green color in confocal images indicates live bacteria, and red color indicates dead bacteria. SEM images and CLSM images are representative of at least three imaged biofilms.

Figures 13A, 13B, 13C:
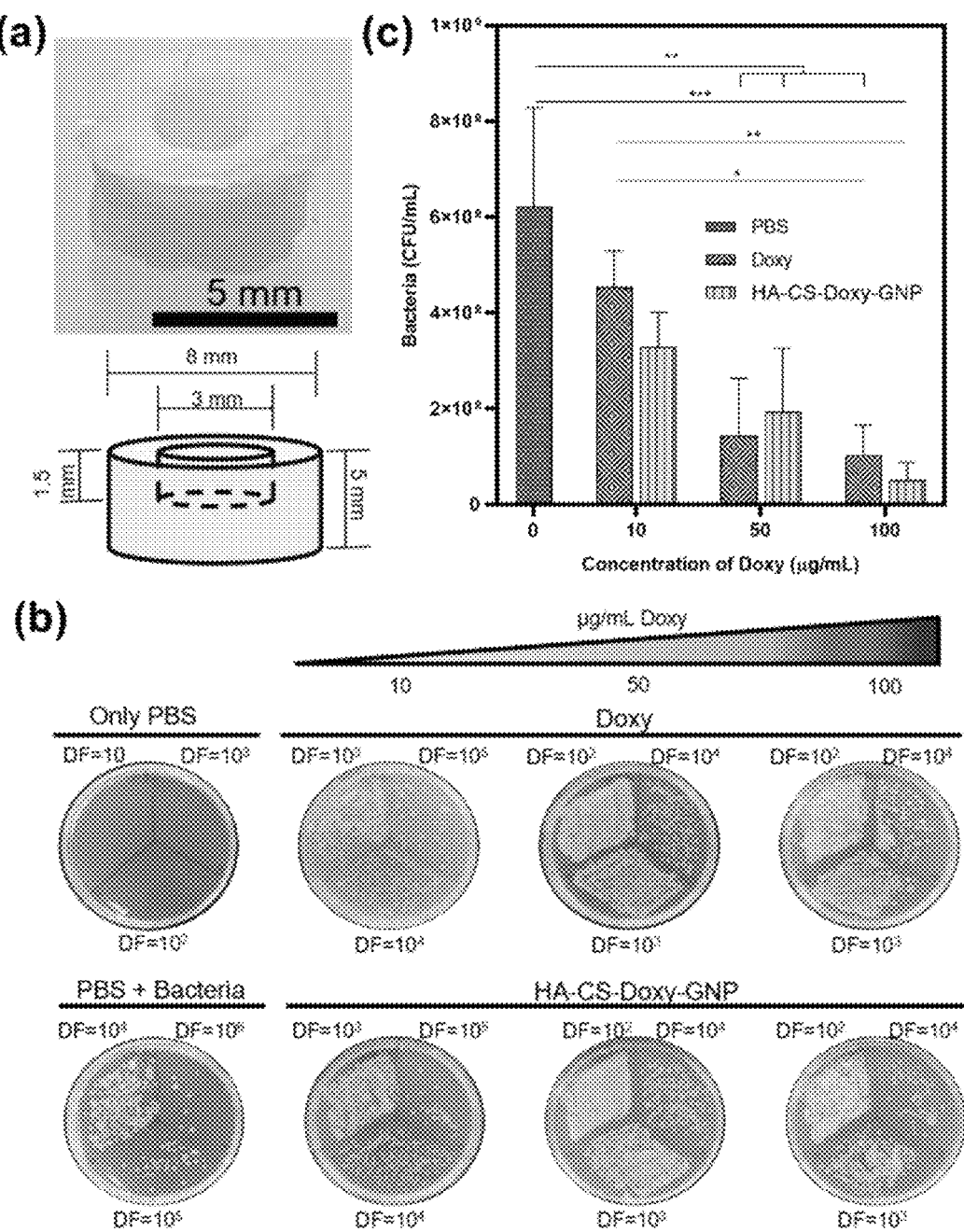

FIGS. 13(a)-(c) Antibacterial efficacy of NPs in an ex vivo pig skin model. FIG. 13(a) Photographs of a pig skin sample. FIG. 13(b) colonies formed on LB agar plate which indicated the viable bacteria in free Doxy and HA-CS-Doxy-GNP treated biofilm. Dilution factor (DF)=final solution volume/volume of stock solution. FIG. 13(c) CFU/mL from free Doxy and HA-CS-Doxy-GNP treated biofilm. Results are shown as mean±standard deviation. Statistical significance (*p<0.05, p<0.01, *p<0.001) between groups is indicated using two-way ANOVA with Tukey's post hoc analysis; n=3. Images of CFU on agar are representatives of at least three repeats.

Figure 14:
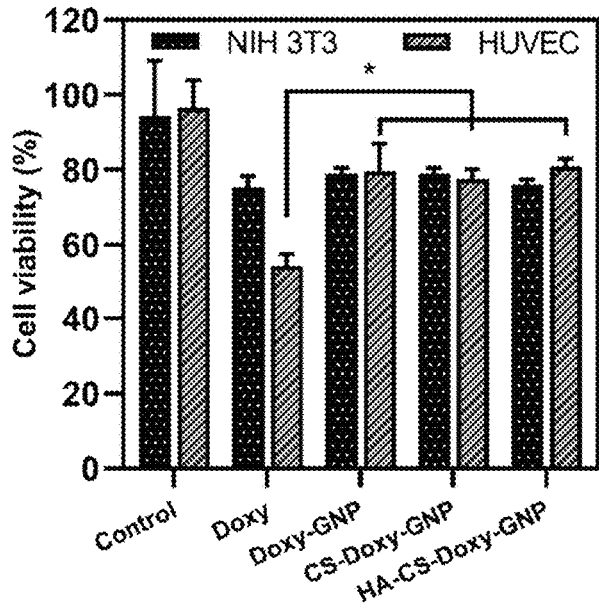

FIG. 14 Cytocompatibility of NPs. Normalized HUVEC and NIH 3T3 cell viability upon exposure to media incubated with free Doxy and Doxy loaded NPs (containing 50 μg/mL Doxy) for 24 h. Results are shown as mean±standard deviation. Statistical significance (*p<0.05) between groups is indicated using two-way ANOVA with Tukey's post hoc analysis; n=3.

FIGS. 15(a)-(d) Hemolysis assay. BRBCs exposed to FIG. 15(a) blank NPs and FIG. 15(b) Doxy loaded NPs at different concentrations. HRBCs exposed to FIG. 15(c) blank NPs and FIG. 15(d) Doxy loaded at different concentrations. Results are shown as mean±standard deviation; n=3.

DETAILED DESCRIPTION

The present disclosure provides methods of designing and using nanoparticles to deliver a payload, such as an antibiotic or drug or diagnostic agent. According to aspects described herein, nanoparticles are designed and used to treat bacterial biofilms in a manner to prevent and/or inhibit and/or eradicate bacterial biofilms. The nanoparticles are designed to be responsive to one or more enzymes or one or more conditions of the biofilms so as to cause a layer of the nanoparticle to degrade thereby exposing a layer or core of the nanoparticle. The layer of the nanoparticle is designed to protect the core until the nanoparticle enters the biofilm wherein the layer is degraded to expose the core. The core then releases a payload agent such as a drug or an antibiotic. According to one aspect, the payload agent can be incorporated into pores of a core or layer or otherwise mixed with the materials forming the core or later and/or may be conjugated or covalently linked or bound to the material forming the core or layer. Such methods of "loading" a core or layer with an active ingredient are known to those of skill in the art. Accordingly, the present disclosure provides a nanoparticle drug delivery system that responds to one or more enzymes or one or more conditions of the biofilm whereby the nanoparticle enters the biofilm, degrades within the biofilm and releases a payload agent, such as an antibiotic to kill the bacteria and prevent the bacteria from creating biofilm. It is an aspect of the present disclosure that the nanoparticle can be designed to take advantage of the enzymes or conditions created by a particular target bacteria. Accordingly, the nanoparticles can be tailored to target particular bacteria based on enzymes or pH conditions created by the particular bacteria, and their biofilms, for destruction.

The present disclosure recognizes that the microenvironment of bacterial infection sites is unlike that in normal tissue in terms of the concentration or composition of various substances. See D. Hu, Y. Deng, F. Jia, Q. Jin and J. Ji, *ACS Nano*, 2020, 14, 347-35; C. Wang, W. Zhao, B. Cao, Z. Wang, Q. Zhou, S. Lu, L. Lu, M. Zhan and X. Hu, *Chemistry of Materials*, 2020, 32, 7725-7738; Y. Liu, A. Lin, J. Liu, X. Chen, X. Zhu, Y. Gong, G. Yuan, L. Chen and J. Liu, *ACS Applied Materials & Interfaces*, 2019, 11, 26590-26606; D. Alkekhia, H. Safford, S. Shukla, R. Hopson and A. Shukla, *Chem. Commun.*, 2020, 56, 11098-11101; D. Pornpattananangkul, L. Zhang, S. Olson, S. Aryal, M. Obonyo, K. Vecchio, C.-M. Huang and L. Zhang, *Journal of the American Chemical Society*, 2011, 133, 4132-4139.

For example, lower pH is often found at bacterial infection sites. See S. Fulaz, D. Hiebner, C. H. N. Barros, H.

Devlin, S. Vitale, L. Quinn and E. Casey, *ACS Applied Materials & Interfaces*, 2019, 11, 32679-32688. The localized acidic biofilm microenvironment results from the production of acidic by-products during bacterial metabolism. See A. M. Scharnow, A. E. Solinski and W. M. Wuest, *Med. Chem. Commun.*, 2019, 10, 1057-1067. Overexpression of proteases also occurs at the infection sites. See G.-B. Qi, D. Zhang, F.-H. Liu, Z.-Y. Qiao and H. Wang, *Advanced Materials*, 2017, 29, 1703461; L.-L. Li, H.-L. Ma, G.-B. Qi, D. Zhang, F. Yu, Z. Hu and H. Wang, *Advanced Materials*, 2016, 28, 254-262; X. Wang, J. Wu, P. Li, L. Wang, J. Zhou, G. Zhang, X. Li, B. Hu and X. Xing, *ACS Applied Materials & Interfaces*, 2018, 10, 34905-34915. For example, bacterial gelatinases contribute to biofilm formation and virulence through degradation of a broad range of host substrates. See L. R. Thurlow, V. C. Thomas, S. Narayanan, S. Olson, S. D. Fleming and L. E. Hancock, *Infection and Immunity*, 2010, 78, 4936-4943. Another class of common enzyme found at the infection sites are hyaluronidases which are virulence factors that are involved in the invasion, and penetration of tissues in bacterial infection. See W. L. Hynes and S. L. Walton, *FEMS Microbiology Letters*, 2000, 183, 201-207.

According to the present disclosure, nanoparticles are designed based on these biofilm environment features using materials responsive to these biofilm environment features. According to one aspect, a nanoparticle is provided which includes a core. The core may include a treatment agent, such as an antibiotic. The core may have an antibiotic and a material responsive to an enzyme which degrades the material. When the core is degraded, the treatment material is released. According to one aspect, the nanoparticle includes a layer of a material responsive to an enzyme produced by the bacteria which degrades the material. The layer may include a treatment agent, such as an antibiotic. When the layer is degraded, the treatment material is released. According to one aspect, the nanoparticle includes a layer of a material responsive to a pH created by the bacteria such that the material swells in response to the pH. The layer may include a treatment agent, such as an antibiotic. According to one aspect, when the layer swells, the treatment material is released. According to one aspect, when the layer swells, the swelling provides access through the layer of an environmental condition to an underlying layer or core.

According to one aspect, the present disclosure is directed to a nanoparticle including various materials which respond to the environment of the bacterial biofilm. The materials can be degraded so as to be removed to expose an underlying layer or core, or the core itself may be degraded. A treatment agent or agents may be in any layer or core, and accordingly be released. The materials can be swelled to release a treatment agent or allow enzymes to penetrate the materials to an underlying layer or core. According to one aspect, the present disclosure is directed to the targeted penetration and destruction of bacterial biofilms wherein a nanoparticle including a core and one or more layers is responsive to a condition of the bacterial biofilm to allow penetration of the nanoparticle into the bacterial biofilm and release of a treatment agent, such as an antibiotic.

Figure 1:
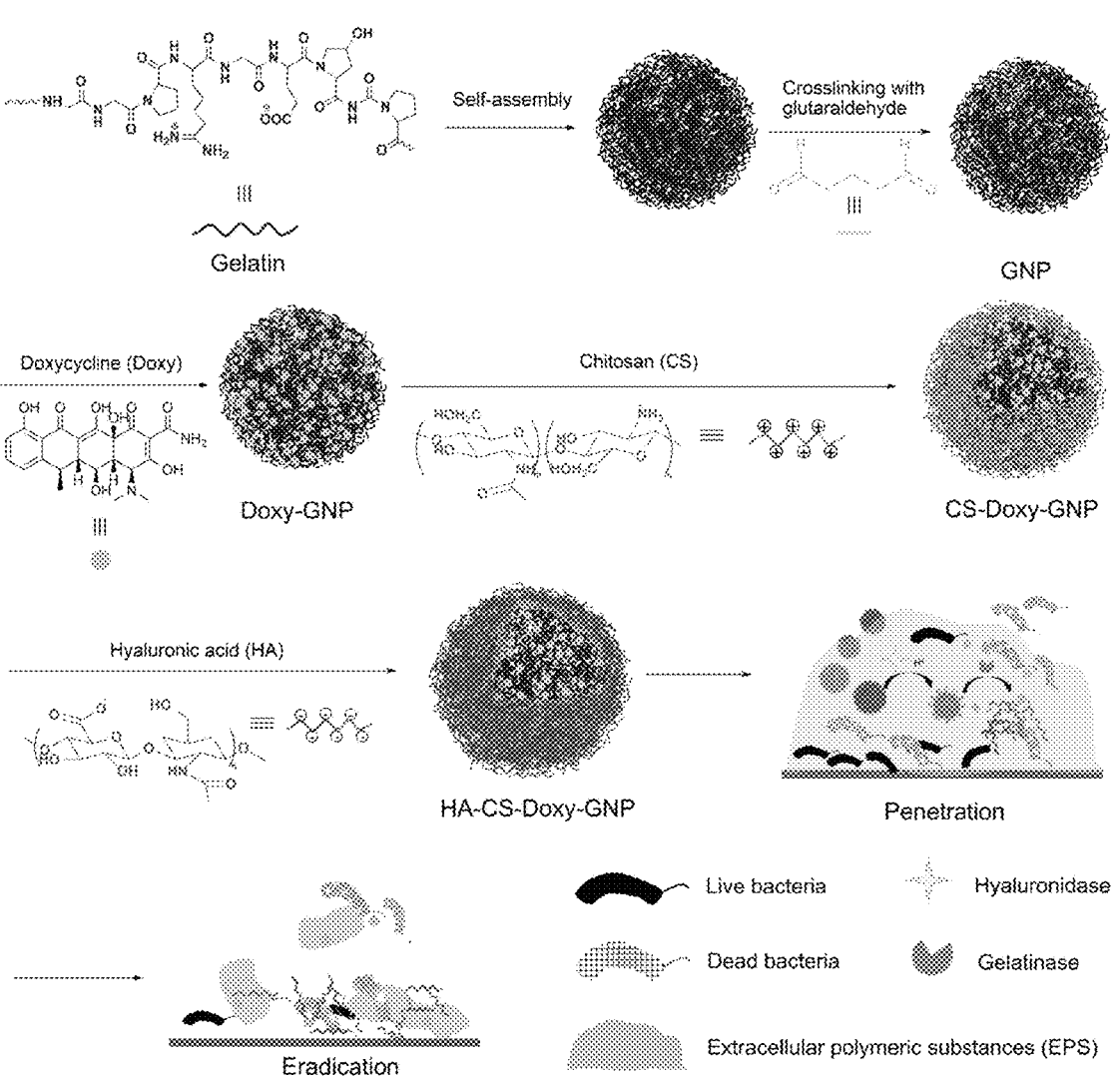
FIG. 1. Schematic of synthesis and antibiofilm mechanism of bacteria responsive HA and CS biopolymer-coated GNPs. HA-CS-Doxy-GNP is fabricated via electrostatic interaction between Doxy-GNP and opposite charged polymers. Bacteria in biofilms metabolically secrete hyaluronidase and acidic metabolites, which promotes the degradation of outermost HA layer and the exposure of CS layer. CS layer becomes positive charge at acidic environment, which enhances the interaction between NPs and bacteria. The loaded Doxy is released when the gelatin core is degraded by bacterial gelatinase.

According to one aspect, a nanoparticle active agent delivery system, such as a drug, antibiotic or diagnostic agent is described that responds to both bacterial enzymes and pH. According to one embodiment, a gelatin core is coated with an outer layer of hyaluronic acid (HA) and an inner layer of chitosan (CS). According to one aspect, the core includes an antibiotic. As depicted in FIG. 1, the nanoparticle is used to deliver the antibiotic to the bacteria within a bacterial biofilm. Gelatin nanoparticles used herein may be those described in drug delivery systems such as P. S. O. Victoria and Speiser, U.K Patent GB1516348, 1978 and R. C. Oppenheim, J. J. Marty and P. Speiser, U.S. Pat. No. 4,107,288, each of which is hereby incorporated herein by reference in its entirety. Various surface modifications which may be useful to incorporate targeting agents, increase nanoparticle NP stability, and control loading and/or release are described in A. Lin, Y. Liu, X. Zhu, X. Chen, J. Liu, Y. Zhou, X. Qin and J. Liu, *ACS Nano,* 2019, 13, 13965-13984; L.-L. Li, J.-H. Xu, G.-B. Qi, X. Zhao, F. Yu and H. Wang, *ACS Nano,* 2014, 8, 4975-4983; J. Su, R. Zhang, Y. Lian, Z. Kamal, Z. Cheng, Y. Qiu and M. Qiu, *Pharmaceutics,* 2019, 11, 93; S. Kirar, N. S. Thakur, J. K. Laha and U. C. Banerjee, *ACS Applied Bio Materials,* 2019, 2, 4202-4212; S. Balthasar, K. Michaelis, N. Dinauer, H. v. Briesen, J. Kreuter and K. Langer, *Biomaterials,* 2005, 26, 2723-2732; T. G. Shutava, S. S. Balkundi, P. Vangala, J. J. Steffan, R. L. Bigelow, J. A. Cardelli, D. P. O'Neal and Y. M. Lvov, *ACS Nano,* 2009, 3, 1877-1885; X.-h. Tian, F. Wei, T.-x. Wang, D. Wang, J. Wang, X.-n. Lin, P. Wang and L. Ren, *Materials Letters,* 2012, 68, 94-96 each of which is hereby incorporated herein by reference in its entirety.

According to one aspect, a layer of a polycation, such as chitosan, is provided on a gelatin core including an antibiotic. A layer of a polyanion, such as hyaluronic acid, is provided over the layer of the polycation. Such layers can be sequentially deposited on the surface of a gelatin core or nanoparticle by a layer-by-layer (LbL) coating method known to those of skill in the art. According to one aspect, the resulting nanoparticle is capable of being administered systemically or topically and will eventually target and penetrate a bacterial biofilm within the individual. The nanoparticle is responsive to conditions created by and/or associated with the biofilm to release the antibiotic within the biofilm.

Without wishing to be bound by scientific theory, under neutral physiological conditions, the net negative charge of the hyaluronic acid on the exterior of the nanoparticle enhances blood circulation residence times when introduced systemically. See E. Blanco, H. Shen and M. Ferrari, *Nature Biotechnology,* 2015, 33, 941-951; M. J. Mitchell, M. M. Billingsley, R. M. Haley, M. E. Wechsler, N. A. Peppas and R. Langer, *Nature Reviews Drug Discovery,* 2021, 20, 101-124. Without wishing to be bound by scientific theory, the water channels present in biofilms can allow nanoparticle entry into the biofilm structure. See P. Stoodley, D. Debeer, and Z. Lewandowski, *Appl Environ Microbiol.* 1994, 60, 2711-2716; K. Quan, J. Hou, Z. Zhang, Y. Ren, B. W. Peterson, H. C. Flemming, C. Mayer, H. J. Busscher, H. C. van der Mei, *Critical Reviews in Microbiology,* 2021. Without wishing to be bound by scientific theory, at biofilm infection sites, bacterial hyaluronidases will degrade the outmost hyaluronic acid layer exposing the underlying chitosan layer which has a net positive charge. The nanoparticles will then become positively charged and have greater ability to attach to biofilm bacteria and certain extracellular polymeric substances, which have net negative charge. See Z. V. Feng, I. L. Gunsolus, T. A. Qiu, K. R. Hurley, L. H. Nyberg, H. Frew, K. P. Johnson, A. M. Vartanian, L. M. Jacob, S. E. Lohse, M. D. Torelli, R. J. Hamers, C. J. Murphy and C. L. Haynes, *Chem. Sci.,* 2015, 6, 5186-5196. Without wishing to be bound by scientific theory, the acidic biofilm microenvironment will cause the chitosan layer to swell thereby providing bacterial gelatinases greater access to the gelatin core. See W. Wang, X. Hao, S. Chen, Z. Yang, C. Wang, R. Yan, X. Zhang, H. Liu, Q. Shao and Z. Guo, *Polymer,* 2018, 158, 223-230; S.-M. Jung, G. H. Yoon, H. C.

Lee, M. H. Jung, S. I. Yu, S. J. Yeon, S. K. Min, Y. S. Kwon, J. H. Hwang and H. S. Shin, *Scientific Reports,* 2015, 5, 18089. Without wishing to be bound by scientific theory, degradation of the gelatin core will increase loaded antibiotic release from the gelatin core, leading to efficient bacteria death and biofilm eradication.

According to the present disclosure, an exemplary bacteria to be treated is *Vibrio vulnificus (V. vulnificus)*, which is a gram-negative pathogen that can cause severe wound infections and and lead to sepsis. See C. Baker-Austin and J. D. Oliver, *Environmental Microbiology,* 2018, 20, 423-430. It is to be understood that the present disclosure is not limited to *V. vulnificus*. Instead, the nanoparticles can be designed to treat and/or deliver an antibiotic to biofilms created by any bacteria where the microenvironment of the biofilm is known or can be determined. When the microenvironment is known, a nanoparticle having at least a layer to protect a drug or antibiotic containing layer or core, and a core including a drug or antibiotic can be designed with each being responsive to a condition or environment of the bacterial biofilm. It is contemplated that administration includes systemic and topical administration methods. According to one aspect, the layer to protect a drug or antibiotic containing layer or core is resistant to degradation or dissolution within the administration environment.

According to the examples described later herein, the exemplary gram-negative pathogen *V. vulnificus* can produce biofilms and secretes common enzymes found in biofilm microenvironments. See J. D. Oliver, J. E. Wear, M. B. Thomas, M. Warner and K. Linder, *Diagnostic Microbiology and Infectious Disease,* 1986, 5, 99-111. Doxycycline (Doxy) is one of the commonly used antibiotics for the treatment of *V. vulnificus* related infection. See S. A. Trinh, H. E. Gavin and K. J. F. Satchell, *Antimicrobial Agents and Chemotherapy,* 2017, 61, e01106-17. The examples describe the synthesis and characterization of the physicochemical properties of doxycycline-loaded gelatin nanoparticles (Doxy-GNP), chitosan-coated Doxy-GNP (CS-Doxy-GNP) and hyaluronic acid-coated CS-Doxy-GNP (HA-CS-Doxy-GNP). The antibacterial and antibiofilm efficacy of each was determined. According to aspects of the present disclosure, the nanoparticles described herein target, penetrate, and accumulate within biofilms, and release antibiotic in a controlled manner to eradicate bacterial biofilms.

Exemplary Bacteria

Bacteria according to the present disclosure includes any bacteria which creates a biofilm and into which nanoparticles can be introduced. It is to be understood that the basic concepts of the present disclosure described herein are not limited by bacteria type. Bacteria according to the present disclosure may include one or members of the species *Vibrio, Clostridium, Escherichia, Rhodococcus, Pseudomonas, Bacillus, Lactobacillus Saccharomyces, Acinetobacter, Staphylococcus, Enterobacter, Klebsiella* and *Enterococcus.* A particularly suitable microorganism is *Vibrio vulnificus.*

Exemplary genus and species of bacteria cells for use in the methods described herein include *Acetobacter aurantius, Acinetobacter bitumen, Actinomyces israelii, Agrobacterium radiobacter, Agrobacterium tumefaciens, Anaplasma Anaplasma phagocytophilum, Azorhizobium caulinodans, Azotobacter vinelandii, viridans* streptococci, *Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacteroides, Bacteroides fragilis, Bacteroides gingivalis, Bacteroides melaninogenicus* (also referred to as *Prevotella melaninogenica), Bartonella, Bartonella henselae, Barto-* nella quintana, Bordetella, Bordetella bronchiseptica, Bordetella pertussis, Borrelia burgdorferi, Brucella abortus, Brucella melitensis, Brucella suis, Burkholderia, Burkholderia mallei, Burkholderia pseudomallei, Burkholderia cepacia, Calymmatobacterium granulomatis, Campylobacter, Campylobacter coli, Campylobacter fetus, Campylobacter jejuni, Campylobacter pylori, Chlamydia, Chlamydia trachomatis, Chlamydophila Chlamydophila pneumoniae (also known as Chlamydia pneumoniae) Chlamydophila psittaci (also known as Chlamydia psittaci), Clostridium, Clostridium botulinum, Clostridium difficile, Clostridium perfringens (also known as Clostridium welchii), Clostridium tetani, Corynebacterium, Corynebacterium diphtheriae, Corynebacterium fusiforme, Coxiella burnetii, Ehrlichia chaffeensis, Enterobacter cloacae, Enterococcus, Enterococcus avium, Enterococcus durans, Enterococcus faecalis, Enterococcus faecium, Enterococcus galllinarum, Enterococcus maloratus, Escherichia coli, Francisella tularensis, Fusobacterium nucleatum, Gardnerella vaginalis, Haemophilus, Haemophilus ducreyi, Haemophilus influenzae, Haemophilus parainfluenzae, Haemophilus pertussis, Haemophilus vaginalis, Helicobacter pylori, Klebsiella pneumoniae, Lactobacillus, Lactobacillus acidophilus, Lactobacillus bulgaricus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma, Mycoplasma fermentans, Mycoplasma genitalium, Mycoplasma hominis, Mycoplasma penetrans, Mycoplasma pneumoniae, Neisseria, Neisseria gonorrhoeae, Neisseria meningitidis, Pasteurella, Pasteurella multocida, Pasteurella tularensis, Peptostreptococcus, Porphyromonas gingivalis, Prevotella melaninogenica (also known as Bacteroides melaninogenicus), Pseudomonas aeruginosa, Rhizobium radiobacter, Rickettsia, Rickettsia prowazekii, Rickettsia psittaci, Rickettsia quintana, Rickettsia rickettsii, Rickettsia trachomae, Rochalimaea, Rochalimaea henselae, Rochalimaea quintana, Rothia dentocariosa, Salmonella, Salmonella enteritidis, Salmonella typhi, Salmonella typhimurium, Serratia marcescens, Shigella dysenteriae, Staphylococcus, Staphylococcus aureus, Staphylococcus epidermidis, Stenotrophomonas maltophilia, Streptococcus Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Treponema, Treponema pallidum, Treponema denticola, Vibrio, Vibrio cholerae, Vibrio comma, Vibrio parahaemolyticus, Vibrio vulnificus, Wolbachia, Yersinia, Yersinia enterocolitica, Yersinia pestis, and Yersinia pseudotuberculosis, and other genus and species known to those of skill in the art.

II. Bacterial Conditions or Environments

As described herein, the exemplary bacteria Vibrio vulnificus creates a biofilm having a net negative charge. The biofilm is characterized by an acidic pH and the presence of proteases, such as hyaluronidases and gelatinases. As described herein, nanoparticles are described that respond to the bacterial enzymes and pH. For example, a material which can swell in an acidic pH can be used. A material which can be degraded by a gelatinases can be used. A material which can be degraded by a hyaluronidase can be used. One of skill can design the nanoparticle core and layers to be responsive to one or more conditions of the bacterial biofilm and order the layers to respond to the one or more conditions in series.

Exemplary bacteria and associated enzymes which can be used to degrade certain materials include Salmonella, Shigella, Yersinia, Staphylococcus aureus (S. aureus) MW2 secrete phosphatases and phospholipases, which can be used to degrade polyphosphoester core-crosslinked structures (R. Devinney, O. Steelemortimer and B. B. Finlay, Trends Microbiol., 2000, 8, 29-33; M. H. Xiong, Y. J. Li, Y. Bao, X. Z. Yang, B. Hu and J. Wang, Adv. Mater., 2012, 24, 6175-6180). Pseudomonas aeruginosa (P. aeruginosa), produces lipases which can be used to cleave lipase-sensitive linkages, such as fatty acid esters or anhydrides (V. V. Komnatnyy, W. C. Chiang, T. Tolkernielsen, M. Givskov and T. E. Nielsen, Angew. Chem., Int. Ed., 2014, 53, 439-441). Streptococcus, Staphylococcus, Peptostreptococcus, Propionibacterium, Streptomyces, Clostridium, and V. vulnificus produce hyaluronidases which can degrade hyaluronic acid (X. Ran, Y. Du, Z. Wang, H. Wang, F. Pu, J. Ren and X. Qu, ACS Appl. Mater. Interfaces, 2017, 9, 19717-19724; W. L. Hynes, S. L. Walton, FEMS Microbiology Letters, 2000, 183, 201-207; J. D. Oliver, J. E. Wear, M. B. Thomas, M. Warner, K. Linder, Diagnostic Microbiology and Infectious Disease, 1986, 5, 99-111). Methicillin-resistant S. aureus (MRSA), S. aureus, Proteus vulgaris, Serratia marcescens, P. aeruginosa and V. vulnifcius secrete gelatinase which can degrade gelatin polymer (A. Lin, Y. Liu, X. Zhu, X. Chen, J. Liu, Y. Zhou, X. Qin, and J. Liu, ACS Nano 2019, 13, 13965-13984; L. Li, J. Xu, G. Q, X. Zhao, F. Yu, and H. Wang, ACS Nano 2014, 8, 4975-4983; J. Xu, R. Danehy, H. Cai, Z. Ao, M. Pu, A. Nusawardhana, D. Rowe-Magnus, and F. Guo, ACS Appl. Mater. Interfaces, 2019, 11, 14640-14646). Klebsiella pneumoniae, Escherichia coli, Enterobacter sp., Salmonella sp., Proteus sp., Serratia marcescens, Shigella dysenteriae, P. aeruginosa, and Burkholderia cepacian, Bacillus cereus produce β-lactamases which can degrade β-lactam coupounds integrated in the nanoparticle core or layers (see C. M. Ferreira, W. A. Ferreira, N. C. O. S. Almeida, F. G. Naveca, M. G. V. Barbosa, Brazilian Journal of Microbiology, 2011, 42, 1076-1084; D. Alkekhia, H. Safford, S. Shukla, R. Hopson, A. Shukla, Chem. Commun., 2020, 56, 11098-11101). Exemplary bacteria and associated pH conditions which can be used to swell certain materials include gram-positive (e.g. S. aureus and Streptococcus pyogenes) and gram-negative bacteria (e.g. P. aeruginosa and Escherichia coli) can produce bacterial metabolisms which lead to the increase or decrease of environmental pH. See R. Sheybani, A. Shukla, Biosensors and Bioelectronics, 2017, 92, 425-433.

Exemplary bacteria and associated factors which can be used to affect certain materials include Streptococcus pneumoniae, group A and B streptococci, S. aureus, Escherichia coli, and Mycobacterium tuberculosis can secrete pore-forming toxins which can degrade liposome-based nanoparticles. See Y. Wu, Z. Song, H. Wang and H. Han, Nature Communications, 2019, 10, 4464; F. C. O. Los, T. M. Randis, R. V. Aroian, A. J. Ratner, Microbiol Mol Biol Rev., 2013, 77, 173-207. Streptococcus pneumoniae, Streptococcus oralis, S. aureus can produce $H_2O_2$ which can cleave the reactive oxygen species-sensitive thioketal-linked nanoparticles. See S. F. Erttmann, Nelson O. Gekara, Nature com-

*munications,* 2019, 10, 3493; J. Li, Z. Ding, Y. Li, J. Miao, W. Wang, K. Nundlall and S. Chen, *Materials and Design,* 2020, 195, 109021.

III. Nanoparticles Having Cores and Layers

Exemplary nanoparticles as described herein have a diameter of between 1 and less than 1000 nanometers, between 1 and 500 nm, between 1 and 250 nm, between 1 and 200 nm, between 1 and 150 nm, between 1 and 100 nm although nanoparticles can also have diameters suitable for the particular application. Nanoparticles can have diameters above 100 nanometers and below 1 nanometer. Nanoparticles are usually present as a distribution of diameters.

Method of making nanoparticles as described herein are known to those of skill in the art and include a layer-by-layer assembly method. See D. Alkekhia, P. T. Hammond, and A. Shukla, *Annual Review of Biomedical Engineering,* 2020, 22, 1-24 hereby incorporated by reference in its entirety for description of the layer-by-layer method. Layer-by-layer nanoparticles are modular active agent delivery vehicles that incorporate multiple functional materials through sequential deposition of polyelectrolytes onto charged nanoparticle cores. According to one aspect, the layer by layer technique utilizes electrostatic attraction to create a multilayer buildup on a core.

Nanoparticles having one or more layers can also be produced by other methods known to those of skill in the art relating to microparticles such as emulsion based methods to form hardened cores which may be loaded with an active agent. One or more layers may then be formed on the core using a spray coating technique in a fluidized bed. See for example U.S. Pat. No. 7,157,102.

One of skill will also recognize other methods of making polymeric nanoparticles such as emulsion based solvent evaporation, emulsification/solvent diffusion, salting-out, desolvation and nanoprecipitation. See J. P. Rao, K. E. Geckeler, *Progress in Polymer Science,* 2011, 36, 887-913 hereby incorporated by reference in its entirety for methods of making polymeric nanoparticles. Exemplary methods include a two-step desolvation method or a nanoprecipitation method.

IV. Exemplary Antibiotic Agents

Active agents according to the present disclosure include antibiotics, antimicrobials and other agents known to be toxic to bacteria. An antibiotic is generally understood to refer to an antimicrobial substance active against bacteria. Antibiotics, antimicrobials, and/or antibacterial agents are used to fight bacterial infections, and antibiotic medications are widely used in the treatment and prevention of such infections. They may either kill or inhibit the growth of bacteria, or prevent bacteria from replicating. Antibiotics are commonly classified based on their mechanism of action, chemical structure, or spectrum of activity. Most target bacterial functions or growth processes. Those that target the bacterial cell wall (penicillins and cephalosporins) or the cell membrane (polymyxins), or interfere with essential bacterial enzymes (rifamycins, lipiarmycins, quinolones, and sulfonamides) have bactericidal activities. Protein synthesis inhibitors (macrolides, lincosamides, and tetracyclines) are usually bacteriostatic (with the exception of bactericidal aminoglycosides). Further categorization is based on their target specificity. "Narrow-spectrum" antibiotics target specific types of bacteria, such as gram-negative or gram-positive, whereas broad-spectrum antibiotics affect a wide range of bacteria.

Exemplary antimicrobial agents include amoxicillin, doxycycline, cephalexin, ciprofloxacin, clindamycin, metronidazole, azithromycin, sulfamethoxazole, trimethoprim, clavulanate, and levofloxacin.

Exemplary antimicrobial agents include Vancomycin, Teicoplanin, Linezolid, Daptomycin, Trimethoprim/sulfamethoxazole, Doxycycline, Ceftobiprole, Ceftaroline, Clindamycin, Dalbavancin, Fusidic acid, Mupirocin, Omadacycline, Oritavancin, Tedizolid, Telavancin, Tigecycline, Aminoglycosides, Carbapenems, Ceftazidime, Cefepime, Ceftobiprole, Ceftolozane/tazobactam, Fluoroquinolones, Piperacillin/tazobactam, Ticarcillin/clavulanic acid, Streptogramins, Daptomycin, Amikacin, Gentamicin, Kanamycin, Neomycin, Netilmicin, Tobramycin, Paromomycin, Streptomycin, Spectinomycin, Geldanamycin, Herbimycin, Rifaximin, Ertapenem, Doripenem, Imipenem/Cilastin, Meropenem, Cefadroxil, Cefazolin, Cephradine, Cephapirin, Cephalothin, and Cefalexin Exemplary antimicrobial agents include Amikacin, Gentamicin, Kanamycin, Neomycin, Netilmicin, Tobramycin, Paromomycin, Streptomycin, Spectinomycin(Bs), Ansamycins, Geldanamycin, Herbimycin, Rifaximin, Carbacephem, Loracarbef, Carbapenems, Ertapenem, Doripenem, Imipenem/Cilastatin, Meropenem, Cefaclor, Cefoxitin, Cefotetan, Cefamandole, Cefmetazole, Cefonicid, Loracarbef, Cefprozil, Cefuroxime, Cephalosporins, Cefixime, Cefdinir, Cefditoren, Cefoperazone, Cefotaxime, Cefpodoxime, Ceftazidime, Ceftibuten, Ceftizoxime, Moxalactam, Ceftriaxone, Cephalosporins, Cefepime, Ceftaroline fosamil, Ceftobiprole, Glycopeptides, Teicoplanin, Vancomycin, Telavancin, Dalbavancin, Oritavancin, Lincosamides(Bs), Clindamycin, Lincomycin, Lipopeptide, Daptomycin, Macrolides(Bs), Azithromycin, Clarithromycin, Erythromycin, Roxithromycin, Telithromycin, Spiramycin, Fidaxomicin, Monobactams, Aztreonam, Nitrofurans, Furazolidone, Nitrofurantoin, Oxazolidinones(Bs), Linezolid, Posizolid, Radezolid, Torezolid, Penicillins, Amoxicillin, Ampicillin, Azlocillin, Dicloxacillin, Flucloxacillin, Mezlocillin, Methicillin, Nafcillin, Oxacillin, Penicillin G, Penicillin V, Piperacillin, Temocillin, Ticarcillin, Polypeptides, Bacitracin, Colistin, Polymyxin B, Quinolones/Fluoroquinolones, Ciprofloxacin, Enoxacin, Gatifloxacin, Gemifloxacin, Levofloxacin, Lomefloxacin, Moxifloxacin, Nadifloxacin, Nalidixic acid, Norfloxacin, Ofloxacin, Trovafloxacin, Grepafloxacin, Sparfloxacin, Temafloxacin, Sulfonamides(Bs), Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Trimethoprim-Sulfamethoxazole (Co-trimoxazole) (TMP-SMX), Sulfonamidochrysoidine (archaic), Tetracyclines(Bs), Demeclocycline, Doxycycline, Metacycline, Minocycline, Oxytetracycline, Tetracycline, Drugs against mycobacteria, Clofazimine, Dapsone, Capreomycin, Cycloserine, Ethambutol(Bs), Ethionamide, Isoniazid, Pyrazinamide, Rifampicin, Rifabutin, Rifapentine, Streptomycin, Arsphenamine, Chloramphenicol(Bs), Fosfomycin, Fusidic acid, Metronidazole, Mupirocin, Platensimycin, Quinupristin/Dalfopristin, Thiamphenicol, Tigecycline(Bs), Tinidazole, and Trimethoprim (Bs).

It is to be understood that the above lists are not exhaustive and that each antimicrobial agent in the lists may be more effective against certain bacteria. One of skill will readily be able to identify exemplary known antimicrobials and the bacteria they are effective against.

V. Exemplary Drugs

Exemplary drugs may include any of those known to those of skill in the art to be effective in treating bacterial infections. Such drugs include penicillins, cephalosporins, aminoglycosides, fluoroquinolones, tetracyclines, macrolides and sulfonamides.

VI. Exemplary Diagnostic Agents

Exemplary diagnostic agents include any of those known to those of skill in the art to be detected within the human body. The diagnostic agent is delivered to the bacterial biofilm by the nanoparticles targeting the bacterial biofilm and is detectable within the bacterial biofilm. Such diagnostic agents include dyes/stains and fluorescent agents, imaging agents and radioactive or radiolabeled substances.

VII. Methods of Therapeutic Treatment

The present disclosure describes methods of therapeutically treating a subject, such as an individual, such as a patient, such as a mammal, such as a human, in need thereof for a bacterial infection. The nanoparticles described herein are administered to an individual and penetrate a bacterial biofilm within the individual. The nanoparticles release an antimicrobial agent within the bacterial biofilm thereby treating the individual for the bacterial infection. The term "treating" or "treatment" is intended to include, but is not limited to, the prevention of the growth of a bacterial infection in a subject or inhibition or reduction in the growth of a pre-existing bacterial infection in a subject. In certain embodiments, the bacteria are sensitive to the antimicrobial agent so as to either kill the bacteria, slow or inhibit the growth of the bacteria or prevent its replication.

In accordance with certain examples, nanoparticles as described herein can be incorporated into pharmaceutical compositions suitable for administration. Such pharmaceutical compositions typically comprise the nanoparticles disclosed herein and a pharmaceutically acceptable carrier. As used herein the term "pharmaceutically acceptable carrier" is intended to include any and all solvents, dispersion media, coatings, antibacterial and antifungal agents, isotonic and absorption delaying agents, wound dressings, and the like, compatible with pharmaceutical administration. The use of such media and agents for pharmaceutically active substances is well known in the art. Except insofar as any conventional media or agent is incompatible with the nanoparticles or active agent, use thereof in the compositions is contemplated. Supplementary active compounds can also be incorporated into the compositions.

In accordance with certain examples, a pharmaceutical composition of the invention is formulated to be compatible with its intended route of administration. Such pharmaceutical compositions may be administered by inhalation, transdermally, topically, orally, rectally, transmucosally, intestinally, parenterally, intramuscularly, subcutaneously, intravenously or other suitable methods that will be readily selected by the person of ordinary skill in the art, given the benefit of this disclosure. For example, solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

In accordance with other examples, pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMPHOR ELTM (BASF, Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

In accordance with other examples, sterile injectable solutions can be prepared by incorporating the nanoparticles in the required amount in an appropriate solvent with one or a combination of ingredients enumerated above, as required, followed by filtered sterilization. Generally, dispersions are prepared by incorporating the nanoparticles into a sterile vehicle which contains a basic dispersion medium and the required other ingredients from those enumerated above. In the case of sterile powders for the preparation of sterile injectable solutions, methods of preparation can be vacuum drying and freeze-drying which yields a powder of the nanoparticles plus any additional desired ingredient from a previously sterile-filtered solution thereof.

Oral compositions generally include an inert diluent or an edible carrier. Nanoparticles as described herein can be enclosed in gelatin capsules or compressed into tablets. For the purpose of oral therapeutic administration, the nanoparticles can be incorporated with excipients and used in the form of tablets, troches, or capsules. Oral compositions including the nanoparticles can also be prepared using a fluid carrier for use as a mouthwash, wherein the nanoparticles in the fluid carrier is applied orally and swished and expectorated or swallowed. Pharmaceutically compatible binding agents, and/or adjuvant materials can be included as part of the composition including the nanoparticles. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In at least certain examples, the nanoparticles are prepared with carriers that will protect the nanoparticles against degradation or rapid elimination from the body, such as a controlled release formulation, including implants and microencapsulated delivery systems. Biodegradable, bio-compatible polymers can be used, such as ethylene vinyl acetate, polyanhydrides, polyglycolic acid, collagen, poly-orthoesters, and polylactic acid. Methods for preparation of such formulations will be apparent to those skilled in the art. The materials can also be obtained commercially from Alza Corporation and Nova Pharmaceuticals, Inc.

In accordance with other examples, methods of treating a bacterial infection within a subject are disclosed. In one example, a method involves contacting a biofilm associated with a bacterial infection with nanoparticles including an antimicrobial as described herein. Methods of treating or preventing a bacterial infection can be performed in vitro (e.g., by treating an in vitro or ex vivo surface having a bacterial biofilm thereon with nanoparticles as described herein) or, alternatively, in vivo (e.g., by administering the nanoparticles to a subject in need thereof). As used herein, a subject is intended to include both human and non-human mammals. Examples of non-human mammals include, but are not limited to, non-human primates, horses, cows, goats, sheep, dogs, cats, mice, rats, hamsters, guinea pigs and the like.

The present invention provides for both prophylactic and therapeutic methods of treating a subject for a bacterial infection. In one aspect, the invention provides a method for preventing a bacterial infection in a subject by administering to the subject the nanoparticles as described herein. Administration of prophylactic nanoparticles can occur prior to the manifestation of symptoms of a bacterial infection, such that the bacterial infection is prevented or, alternatively, delayed in its progression.

One embodiment of the present disclosure involves a method of treating a bacterial infection which includes the step of administering a therapeutically and/or prophylacti-cally effective amount of nanoparticles as described herein to a subject. As defined herein, a therapeutically and/or prophylactically effective amount of nanoparticles (i.e., an effective dosage) ranges from about 0.001 to 30 mg/kg body weight, from about 0.01 to 25 mg/kg body weight, from about 0.1 to 20 mg/kg body weight, from about 1 to 10 mg/kg, from about 2 to 9 mg/kg, from about 3 to 8 mg/kg, from about 4 to 7 mg/kg, or from about 5 to 6 mg/kg body weight. The skilled artisan will appreciate that certain factors may influence the dosage required to effectively treat a subject, including but not limited to the severity of the bacterial infection, previous treatments, the general health and/or age of the subject, and other diseases or conditions present. Treatment of a subject with a therapeutically and/or prophylactically effective amount of nanoparticles can include a single treatment or can include a series of treat-ments. It will also be appreciated that the effective dosage of nanoparticles for treatment may increase or decrease over the course of a particular treatment.

VIII. Kits

In accordance with certain other examples, kits for treat-ing bacterial infections in a subject are provided. A "kit" is a collection of parts forming the kit. In one example, the kit may include nanoparticles as described herein including an antimicrobial agent in a vial. The kit may include a phar-maceutically acceptable carrier in a vial. The kit may include nanoparticles in a pharmaceutically acceptable carrier in a vial. In an additional example, the kit may also include instructions for treating bacterial infections in a subject by administering the nanoparticles. In some examples, the kit may also comprise, e.g., a buffering agent, a preservative, or a protein stabilizing agent. In some examples, the kit may include an apparatus for administering the nanoparticles such as a syringe or other apparatus. Other suitable compo-nents for including in the kit will be selected by the person of ordinary skill in the art, given the benefit of this disclo-sure.

The following examples are set forth as being represen-tative of the present disclosure. These examples are not to be construed as limiting the scope of the present disclosure as these and other equivalent embodiments will be apparent in view of the present disclosure, figures and accompanying claims.

Example I

Materials

Gelatin (Type B, bloom number of ~225 g), glutaralde-hyde (50% (w/w) in water), doxycycline hydrochloride (Doxy), chitosan (CS) (≥75% deacetylated), sucrose, type IV collagenase (i.e., gelatinase) from *Clostridium histolyti-cum*, hyaluronidase from bovine testes, 10× Dulbecco's phosphate buffered saline (10×PBS, pH 7.4), acetone, etha-nol (200 proof, anhydrous, 99.5%), sodium chloride (NaCl), glucose and vancomycin were obtained from Sigma-Aldrich (St. Louis, MO). Hyaluronic acid (HA) sodium salt (average molecular weight (MW) 36 KDa) was obtained from Lifecore Biomedical (Chaska, MN). Silicon wafers were purchased from WaferPro (Santa Clara, CA). *V. vulnificus* (ATCC 27562), human umbilical vein endothelial cells (HUVEC) and mouse embryonic fibroblasts (NIH 3T3) were obtained from American Type Culture Collection (ATCC, Manassas, VA). Tryptic soy broth (TSB), FilmTracer SYPRO Ruby biofilm matrix stain, LIVE/DEAD BacLight Bacterial Viability Kit was purchased from Thermo Fisher Scientific (Waltham, MA). Dulbecco's modified Eagle's medium (DMEM) and fetal bovine serum (FBS) were purchased from Gibco-BRL (Grand Island, NY). Penicillin-streptomycin was obtained from Caisson Laboratories (Smithfield, UT). Lennox broth (LB) and crystal violet were purchased from Millipore Sigma (St. Louis, MO). Bacto agar was obtained from BD Biosciences (San Jose, CA). EGM-2 Endothelial Cell Growth Medium-2 BulletKit were purchased from Lonza (Basel, Switzerland). Cell Counting Kit-8 (CCK-8) was purchased from Dojindo Molecular Technologies (Tokyo, Japan). Bovine red blood cells (BRBCs) (10% in 1×PBS) and single donor human red blood cells (HRBCs) washed were purchased from Innova-tive Research (Novi, MI). All chemicals were of analytical reagent quality or high-performance liquid chromatography (HPLC) grade. Ultrapure water (18.2 MW cm Milli-Q, Millipore Sigma, Billerica, MA) was utilized in all experi-ments requiring water. Room temperature (RT) refers to about 23° C.

Example II

Synthesis of Nanoparticles

Gelatin is a natural, biocompatible, biodegradable and inexpensive macromolecule that is considered as an ideal polymer used to build drug delivery systems. See R. Yasmin, M. Shah, S. A. Khan and R. Ali, Nanotechnology Reviews, 2017, 6, 191-207. Gelatin nanoparticles (GNPs) were pre-pared by using a two-step desolvation method. To achieve monodispersed GNPs, the low MW gelatin fraction in the supernatant was discarded during the first desolvation step. The high MW gelatin fraction was then redissolved to form GNPs for the second desolvation step. To efficiently encap-sulate the antibiotic doxycycline (Doxy) into GNPs, the GNP suspension was first lyophilized and then suspended in a Doxy solution for 24 hours with gentle agitation. The nanoparticles (NPs) were washed to remove free Doxy in solution, and then resuspended in water to obtain the Doxy-GNPs. The NPs were resuspended in water to obtain the Doxy-GNP. To further enhance the targeting and responsive properties of this drug delivery system, NPs were coated via adsorption of chitosan (CS) followed by hyaluronic acid (HA) to produce Doxy-GNPs coated with bio-polymer shells.

In further detail, gelatin nanoparticles ("GNPs") were prepared by the two-step desolvation method as previously reported. See A. Lin, Y. Liu, X. Zhu, X. Chen, J. Liu, Y. Zhou, X. Qin and J. Liu, *ACS Nano*, 2019, 13, 13965-13984; J. Xu, R. Danehy, H. Cai, Z. Ao, M. Pu, A. Nusawardhana, D. Rowe-Magnus and F. Guo, *ACS Applied Materials & Interfaces*, 2019, 11, 14640-14646. 1.25 g gelatin powders were dissolved in 25 mL (50 mg/mL) water at 50° C. under stirring (360 rpm). In the first desolvation step, 25 mL acetone was added into the solution dropwise during stirring (360 rpm). After the addition of acetone, the stirring was halted. The gel-like gelatin fractions were precipitated after 15 minutes and the opaque supernatant containing the low molecular weight gelatin was discarded. The sediment was resuspended by adding 25 mL of water at 50° C. while stirring (360 rpm) and the pH was adjusted to 11. Next, 75 mL of acetone was added a flow rate of approximately 1 mL/min to form the gelatin nanoparticles (GNPs) under continuous stirring (600 rpm), inducing the second desolvation process and particle formation. Finally, 150 µL of 25% glutaraldehyde was added dropwise to cross-link the particles. The solution was left to stir for 18 hours (h) at RT. The GNPs obtained were collected and washed three times with water. All NP collection and wash steps were carried out via centrifugation at RT (16,000×g for 20 minute).

Doxy-loaded GNPs (Doxy-GNP) were synthesized by mixing varying ratios of lyophilized GNPs with Doxy solution (15 mg/mL). After swelling and loading of Doxy into GNPs for 24 hours at RT, the NPs were washed three times with water at RT to remove unloaded free Doxy. To form the chitosan (CS)/hyaluronic acid (HA) (CS/HA) bilayer coating on Doxy-GNPs, first the CS layer was adsorbed by gradual addition of 10 mL of 1 mg/mL Doxy-GNP suspension in water (Ph 6) to 10 mL of 1 mg/mL aqueous CS (pH 6) under stirring (500 rpm). After stirring for 1 hour, the CS-Doxy-GNPs were collected and washed three times with water, followed by a final resuspension in 10 mL of water (pH 6). The HA layer was fabricated by adding 10 mL of 1 mg/mL aqueous HA (pH 6) to the CS-Doxy-GNP suspension dropwise under stirring (500 rpm) for 1 hour. The resulting HA-CS-Doxy-GNPs were collected and washed three times with water. All washes were collected for quantification of Doxy loss during bilayer assembly.

Example III

Characterization of Nanoparticle Size and Charge

The hydrodynamic diameter and zeta (0 potential of GNPs, CS-GNPs, HA-CS-GNPs with or without Doxy were measured at 25° C. using dynamic light scattering (DLS) using Zetasizer (Zetasizer Nano ZS90, Malvern Instruments, UK) operating at a scattering angle of 90°.

Environmental scanning electron microscopy (ESEM) was used to further investigate the morphology and structure of these nanoparticles (NPs). Samples were prepared by placing 10 µL of diluted NPs suspension on the surface of silica wafers (0.5 cm×0.5 cm) and allowing them to dry under RT for 24 hours. These samples were sputter-coated with gold-palladium for 2 min (18 nm coating thickness) under argon. Samples were examined using an ESEM (Quattro S, Thermo Fisher Scientific, Waltham, MA) operated at 10 kV.

Figures 2A, 2B:
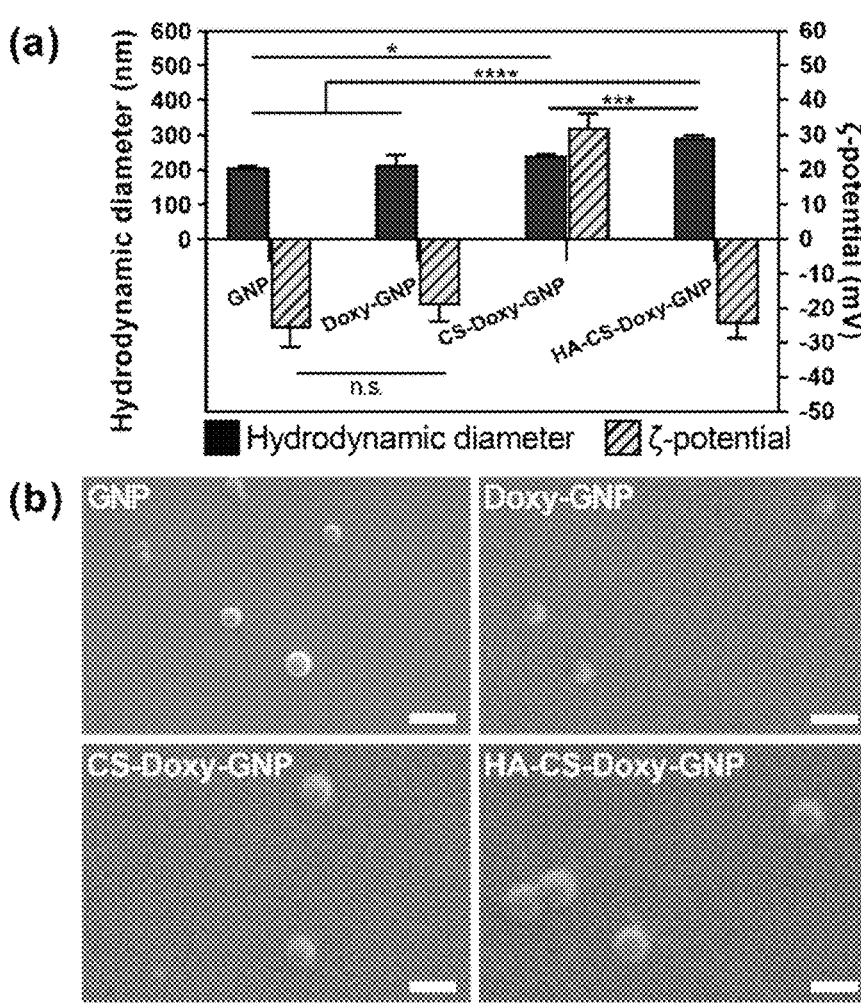
FIGS. 2(a)-(b). The characterization of NPs.

The morphology and size of GNP, Doxy-GNP, CS-Doxy-GNP and HA-CS-Doxy-GNP were investigated. As shown in FIG. 2(*a*), the average hydrodynamic diameter increased with additional polymer coating layers, from about 215 nm for Doxy-GNP to 243 nm and 292 nm for CS-Doxy-GNP and HA-CS-Doxy-GNP, respectively. SEM analysis was used to obtain images to measure the particle size analysis and shape, indicating that the GNP, Doxy-GNP, CS-Doxy-GNP and HA-CS-Doxy-GNP were spherical, with the average size about 207, 215, 275 and 303 nm (FIG. 2(*b*)). The ζ potential value of Doxy-GNP, CS-Doxy-GNP and HA-CS-Doxy-GNP surface charge changes from about −19.1 mV to +32.2 mV and −24.6 mV of over coating process (FIG. 2(*a*)). There was no significant difference in the size and potential value between GNP and Doxy-GNP. However, after CS coating, the mean potential of NPs increased dramatically. Since CS is a cationic polymer containing amino groups, it forms hydrogen bonds with surfaces of the negative Doxy-GNP, causing the CS-Doxy-GNP to have a positive potential. After coating with HA which contains carboxyl groups, the surface charge changed to negative charge with a significant increase in size. The size increase and surface charge reversal during fabrication process indicate the successful sequential deposition of polycation CS and polyanion HA.

Example IV

Spectral Scan of Doxy and Standard Curve

Figures 3A, 3B:
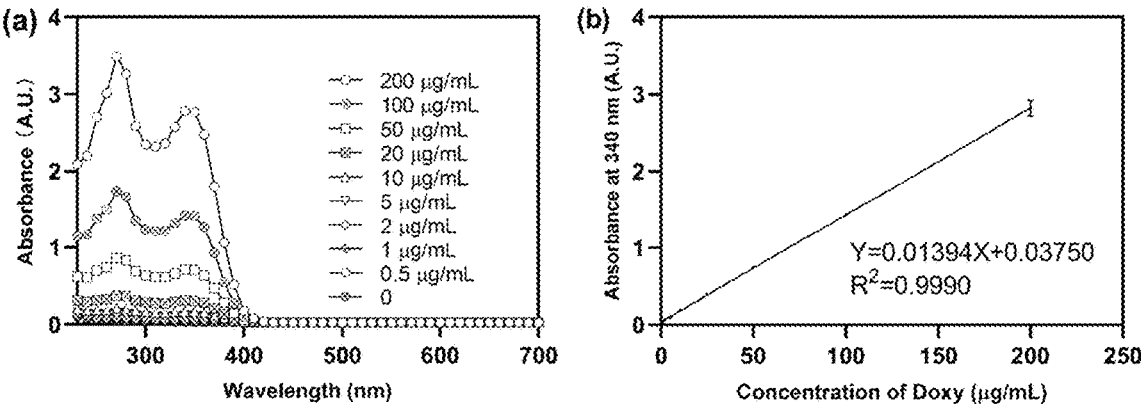
FIGS. 3(a)-(b) Absorbance spectra of Doxy.

200 µL Doxy aqueous solutions with different concentrations (from 0.5 to 200 µg/mL) were measured in 96-well clear flat bottom UV-transparent microplate by a plate reader. The absorbance at 340 nm was used to calculated for linear relationship with Doxy concentrations. FIG. 3(*a*) and FIG. 3(*b*) depict the absorbance spectra of Doxy. FIG. 3(*a*) depicts a spectral scan of Doxy aqueous solutions with different concentrations. FIG. 3(*b*) depicts linear regions of plots of absorbance at 340 nm as a function of Doxy concentrations. Data are shown as mean±standard deviation (n=3).

Example V

Quantification of Doxy Loading and Release

Encapsulation efficiency (EE %) and drug loading capacity (DL %) of Doxy was determined based on measuring the absorbance of unloaded Doxy in washing solutions using a Cytation 3 microplate reader (BioTek, Winooski, VT) using 96-well clear flat bottom UV-transparent microplates. Serial diluted Doxy solutions were measured to obtain standard curve (see FIG. 3(*a*) and FIG. 3(*b*)). The EE % and DL % were estimated from the following equations.

$$EE\% = \frac{\text{Initial Doxy mass} - \text{Free Doxy mass in supernatant}}{\text{Initial Doxy mass}} \times 100\%$$

$$DL\% = \frac{\text{Initial Doxy mass} - \text{Free Doxy mass in supernatant}}{\text{Final } NPs \text{ mass}} \times 100\%$$

The release of Doxy from the different NP formulations was investigated in various conditions, including 1×PBS at pH 7.4, 1×PBS at pH 5, 100 µg/mL gelatinase in 1×PBS at pH 5, 150 U/mL hyaluronidase in 1×PBS at pH 5 or V.

*vulnificus* conditioned culture medium at pH 5.5. Note, 1 U of hyaluronidase is defined by the manufacturer as causing a 0.330% change in transmittance at 600 nm per minute at pH 5.35 at 37° C. in a 2.0 mL reaction mixture (0.015% (w/v) hyaluronic acid, 150 mM sodium phosphate, and 2-5 U of hyaluronidase) over 45 minutes. The different NP formulations (10 mg/mL) were incubated in 1 mL of of each of these solutions by using a Float-A-Lyzer G2 dialysis device (3.5-5 KDa molecular weight cut-off (MWCO), 1 mL, Repligen, Waltham, MA) at 37° C. for 48 hours with gentle agitation at 100 rpm. At predetermined intervals, 200 μL solution was removed from the incubation bath to analyze for Doxy content via measuring absorbance; an equal volume of fresh incubation medium was supplied.

Figures 4A, 4B:
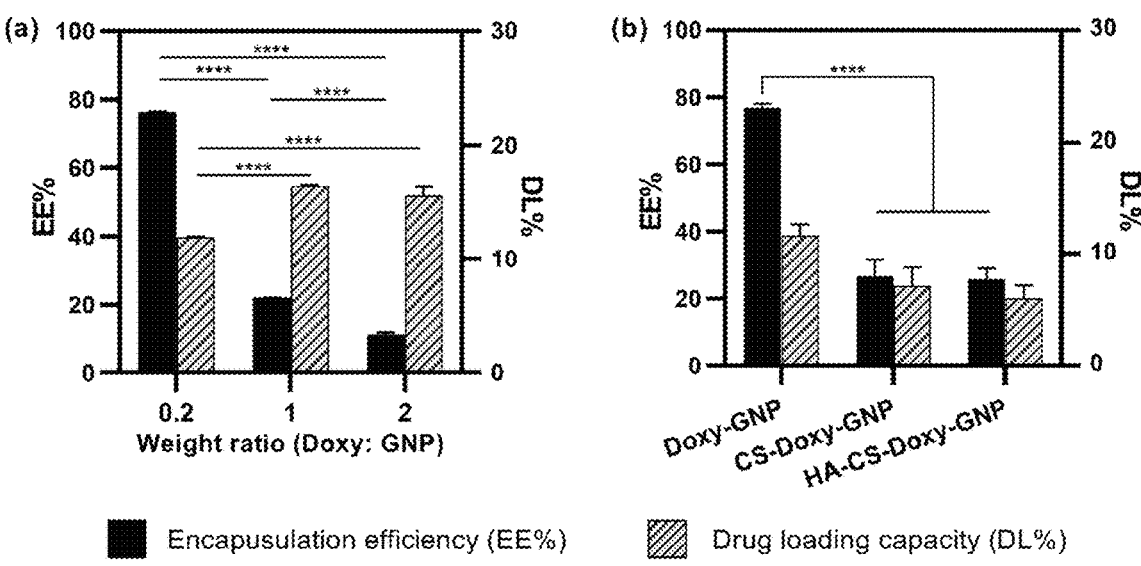
FIG. 4(a) Encapsulation efficiency (EE %) and FIG. 4(b) drug loading (DL %) of NPs. GNPs with a weight ratio of Doxy to GNPs of 0.2, 1.0, and 2. Results are shown as mean±standard deviation. Statistical significance (****p<0.0001) between groups is indicated using two-way ANOVA with Tukey's post hoc analysis; n=3.

EE % and DL % of Doxy-GNP varied based on the adding weight ratio of Doxy to GNP (see FIG. 4(*a*)). Serial diluted Doxy solutions were measured to obtain standard curve. When the concentration of Doxy remained constant, the EE % decreased and DL % increased with the decrease of added GNP. The optimal weight ratio of Doxy to GNP was determined to be 0.2 (w/w) with EE % being about 76.9% and DL % being 11.7%. After coating with CS and HA, the EE % and DL % of HA-CS-Doxy-GNP decreased to about 25.8% and about 6.0%, respectively (see FIG. 4(*b*)).

Figures 5A, 5B, 5C, 5D, 5E, 5F:
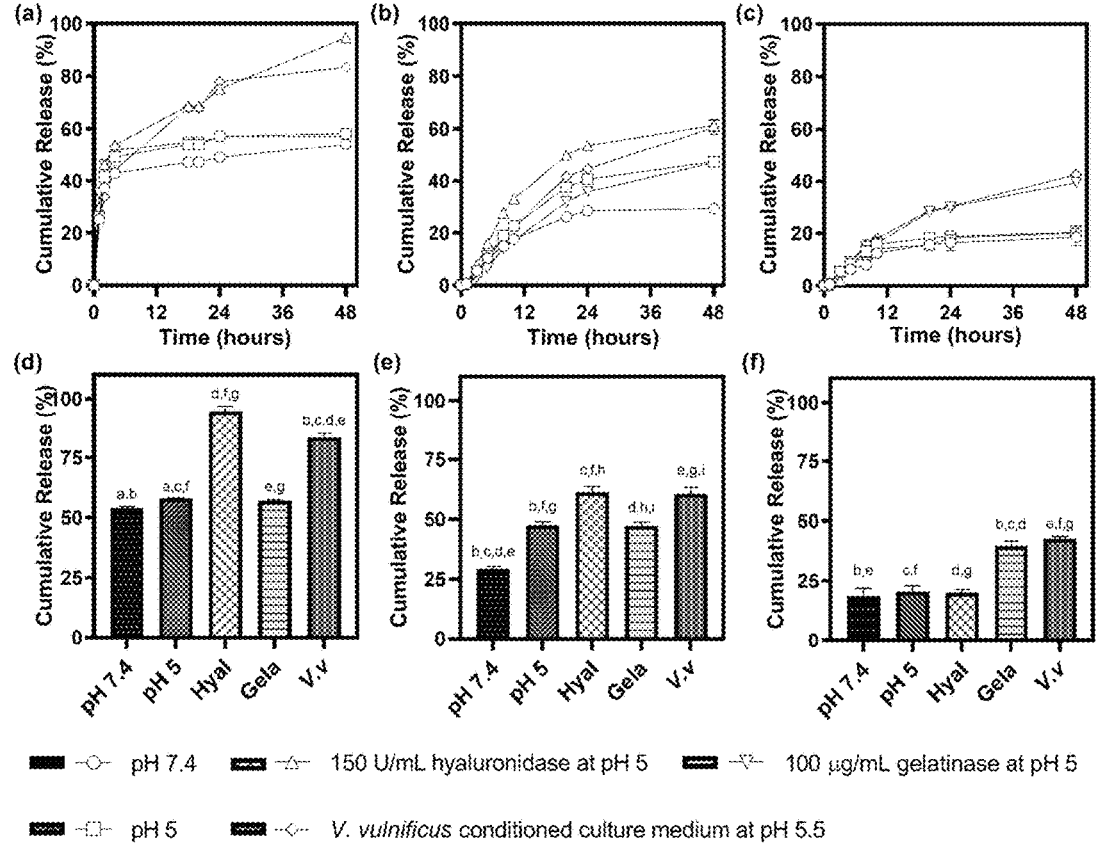
FIGS. 5(a)-(f) Drug release of NPs. In vitro Doxy release from FIG. 5(a) Doxy-GNPs, FIG. 5(b)CS-Doxy-GNPs and FIG. 5(c) HA-CS-Doxy-GNPs in 1×PBS at pH 7.4, 1×PBS at pH 5, gelatinase in 1×PBS at pH 5, hyaluronidase in 1×PBS at pH 5, and V. vulnificus conditioned culture medium at pH 5.5 at 37° C. for 48 h. The in vitro cumulative drug release at 48 h FIG. 5(d) Doxy-GNPs, FIG. 5(e)CS-Doxy-GNPs and FIG. 5(f) HA-CS-Doxy-GNPs in the above conditions. Results are shown as mean±standard deviation. Statistical significance between conditions is indicated by matching letters using one-way ANOVA with Tukey post-hoc analysis. The letter a represents p<0.05. The other letters (b, c, d, e, f, g) represent p<0.0001; n=3.

Doxy release was quantified from Doxy-GNPs, CS-Doxy-GNPs and HACS-Doxy-GNPs under various conditions, including gelatinase in 1×PBS at pH 5, 1×PBS at pH 7.4, 1×PBS at pH 5, hyaluronidase in 1×PBS at pH 5, and *V. vulnificus* conditioned culture medium at pH 5.5 (FIGS. 5(*a*)-5(*f*)). During the growth of bacteria, the amount of enzymes produced varies. See A. Y. Lee, K. T. Akers, M. Collier, L. Li, A. Z. Eisen and J. L. *Seltzer, Proceedings of the National Academy of Sciences,* 1997, 94, 4424-4429; D. Pecharki, F. C. Petersen and A. A. Scheie, *Microbiology,* 2008, 154, 932-938. Here, the concentrations used to determine drug release were chosen as representatives based on other similar reported works. See Y. Sun, H. Qin, Z. Yan, C. Zhao, J. Ren and X. Qu, *Advanced Functional Materials,* 2019, 29, 1808222; H. Ji, K. Dong, Z. Yan, C. Ding, Z. Chen, J. Ren and X. Qu, *Small,* 2016, 12, 6200-6206. As shown in (FIG. 5(*a*)), Doxy-GNPs exhibited a fast release rate at all conditions, releasing more than 40% of the encapsulated Doxy within 4 hours. After 5 hours, additional release was only observed in gelatinase or conditioned media resulting in greater than 80% cumulative Doxy release from Doxy-GNP after 48 hours (FIG. 5(*d*)). The addition of the CS layer in the CS-Doxy-GNPs reduced the burst release observed from Doxy-GNPs at 4 hours from about 40% down to about 10% (FIG. 5(*b*)). Over time, low pH conditions resulted in greater drug release from CS-Doxy-GNPs compared to other release conditions, likely due to CS protonation and swelling. After 48 hours (FIG. 5(*d*)), CS-Doxy-GNP in 1×PBS at pH 5 and hyaluronidase in 1×PBS at pH 5 led to about 45% Doxy release compared to about 30% Doxy release in 1×PBS at pH 7.4. The presence of gelatinase, including gelatinase in 1×PBS at pH 5 and in conditioned media extended the drug release, resulting in about 60% Doxy release over 48 hours. The addition of the HA layer produced a similar release as CS-Doxy-GNPs of about 20% Doxy over the first 10 hours (FIG. 5(*c*)). After that, the different pH conditions and gelatinase in 1×PBS did not cause further release from HA-CS-Doxy-GNPs. However, hyaluronidase treatment and conditioned media led to an extended release over the 48 hours up to about 40% release (FIG. 5(*e*)). Together, these results demonstrated that the presence of hyaluronidases, acidic conditions, or gelatinases can control Doxy release from HA-CS-Doxy-GNPs.

Example VI

Morphology Characterization of Planktonic
    *V. vulnificus* and *V. vulnificus* Biofilm by SEM
    2-day aged *V. vulnificus* biofilms were formed on silicon wafer surfaces (0.5 cm×0.5 cm) which were placed in the wells of 24-well plates. Then the biofilms were gently washed three times in 1×PBS and fixed with 2.5% glutaraldehyde at 4° C. for 4 hours. After the biofilms were washed with 1×PBS, samples were dehydrated gradually through a series of ethanol concentrations of 50%, 60%, 70%, 90% and 100% (10 minutes each). The dehydrated biofilms were lyophilized, then imaged by SEM after sputter coating with gold and palladium. FIG. 6(*a*) depict an SEM image of planktonic *V. vulnificus*. FIG. 6(*b*) depict and SEM image of *V. vulnificus* biofilm on a silicon wafer.

Example VII

Characterization of the Formation and Microenvironment of *V. vulnificus* Biofilm. *V. vulnificus* Biofilm Formation at Different Conditions
    The planktonic *V. vulnificus* in LB medium were incubated overnight with shaking (100 rpm) at 37° C. Overnight cultured bacteria suspension was dilute 1:500 in LBS, LBS with 1% w/v glucose and LBS at pH 5.5. Then biofilms were formed in 96-well plates by static incubation at 37° C. for different times (24 hours or 48 hours). The biofilm biomass was evaluated using crystal violet staining. All solutions were measured directly except samples from 24 hours. At 24 hours, samples were dilute 10-fold before reading $OD_{570}$.
pH Change of *V. vulnificus* Biofilm at Different Conditions
    *Vibrio* biofilms were formed as described above with minor modifications. The biofilms were formed in culture tubes instead of a 96-well plate. The biofilm was disturbed by sonication. First a continuous vortex for 1 minute at full speed was performed. Then, probe based sonication was conducted at 26 W for 60 seconds. The tube was kept on ice to prevent heating due to sonication. Another round of continuous vortex for 1 minute at full speed was carried out. At 0 hours, 24 hours and 48 hours, the biofilm formed at different conditions was sonicated to obtain homogenized bacterial suspensions. The pH of each homogenized bacterial suspension was taken by pH meter.
Gelatin Hydrolysis Test
    LB with 3% w/v gelatin medium were autoclaved for 15 minutes at 121° C. The gelatin LB medium was stored at 4° C. after cooling. *V. vulnificus* frozen stock at −80° C. was obtained and then spread on the LB agar plate by toothpick followed by inoculation at 37° C. for 24 hours for the growth of a single colony. The gelatin LB medium was warmed at 37° C. in a water bath to obtain a liquid medium. 4 mL of the medium was dispensed into two culture tubes. The tubes were cooled to 4° C. to solidify the gelatin LB medium. Several well-isolated colonies were selected. The nutrient gelatin medium was inoculated with a test inoculum by stabbing 4 to 5 times about a half inch into the medium. The test and an un-inoculated tube were incubated for 24 hours at 37° C. After 24 hours, the culture tubes were taken from the incubator and placed vertically in an ice bath for 30 minutes. The phase of the medium was observed. Liquid medium resulted where gelatin was hydrolyzed, indicating the present of gelatinase.

A Plate Method for the Detection of Hyaluronidase

Hyaluronidase activity was determined using the simple plate assay. LB broth (6 g in 120 mL of water) containing 1% (w/v) agarose was autoclaved at 121° C. for 15 minutes. The molten medium was equilibrated to 50° C. prior to the addition of 40 mL of filter-sterilized bovine serum albumin (BSA, 5% w/v prepared in water) and 40 mL of filter-sterilized HA (2 mg/mL prepared in water) both equilibrated to 50° C. This agar (LBHA) was poured to a depth of 2-3 mm. After solidification, plates were stored at 4° C. Overnight cultures of *V. vulnificus* were diluted 1:500 with LB, and 20 µL bacterial suspension were dropped onto LBHA plates. Plates were incubated at 37° C., and observed daily until growth was observed (48 hours). On the day growth was first observed, the plate was flooded with 2 M acetic acid, which binded hyaluronic acid and albumin to form a white precipitate. Hyaluronidase production was considered to have been present if a zone of clearing was observed. FIGS. 7(*a*)-7(*d*) are directed to the characterization of the formation and microenvironment of *V. vulnificus* biofilm. FIG. 7(*a*) depicts a crystal violet assay used to assess the formation of *V. vulnificus* in different conditions, including LBS, LBS with 1% w/v glucose and LBS at pH 5.5. $OD_{570}$ was read to indicate biofilm biomass. All solutions were measured directly except samples from 24 hours. All three conditions at 24 hours were dilute 10-fold before reading $OD_{570}$. Image above each column was taken after extracted crystal violet. FIG. 7(*b*) depicts pH change of *V. vulnificus* biofilms which were formed in different growth media. FIG. 7(*c*) depicts a gelatin hydrolysis test of *V. vulnificus*. FIG. 7(*d*) depicts a plate method for the detection of hyaluronidase.

According to one aspect, the antibiofilm drug delivery systems described herein remain inert at physiological conditions but release a drug or antibiotic under the biofilm microenvironment. *V. vulnificus* was able to form biofilm in various conditions, including including LBS, LBS with 1% w/v glucose and LBS at pH 5.5 (FIG. 7(*a*)). Significantly more *V. vulnificus* biofilm was seen in LBS at pH 5.5. pH of biofilm was also investigated. At 0 hours, 24 hours and 48 hours, the biofilm formed in different media was sonicated to obtain homogenized bacterial suspensions for the pH measurement. As shown in FIG. 7(*b*), pH increased when using LBS and LBS at pH 5.5. The pH of bacterial suspension with LBS with 1% w/v glucose decreased from about 6.8 to about 5.2 along and increasing time to form sufficiently stable biofilm for further study and to mimic the acidic biofilm environment. LB S at pH 5.5 was used. Previous studies showed that *V. vulnificus* can produce various virulence factors, including gelatinase and hyaluronidase. See J. D. Oliver, J. E. Wear, M. B. Thomas, M. Warner and K. Linder, *Diagnostic Microbiology and Infectious Disease,* 1986, 5, 99-111. The production of these two enzymes was confirmed by gelatin hydrolysis test and a plate method. Gelatin dissolves in water at 50° C., solidifies or gels when cooled below 25° C. As seen in FIG. 7(*c*), LB medium containing gelatin and *V. vulnificus* remained liquid after cooling. It indicated that *V. vulnificus* can produce gelatinase. Hyaluronidase activity was determined using the simple plate assay. See R. F. Smith and N. P. Willett, *Applied microbiology,* 1968, 16, 1434-6. A clear zone was observed which indicated the hyaluronidase production from *V. vulnificus* (FIG. 7(*d*)).

Example VIII

Penetration of NPs in Biofilm

Unless otherwise noted, all biofilm experiments utilized the following procedure for the formation of a 48 h matured biofilm. *V. vulnificus* inoculated LB medium was incubated for 18 h with shaking (100 rpm) at 37° C. This bacteria suspension was dilute 1:500 (v/v) in LB media supplemented with 2% w/v NaCl (LB S) at pH 5.5. The optical density of the bacteria suspension at 600 nm ($OD_{600}$) was monitored overtime. Once in its logarithmic growth phase ($OD_{600}$=0.1, which is ~$1.5 \times 10^7$ CFU/mL), biofilms were formed by static incubation of bacteria at 37° C. for 48 hours either in chamber slides of multi-well plates. Every 24 hours, the biofilms were gently washed three times with 1×PBS and add fresh LBS was added.

To assess NP penentration into biofilms, biofilms were formed in 8-well chambered cover glass. After washing with 1×PBS, 1 mg/mL GNPs, CS-GNPs, and HA-CS-GNPs were added to the wells and incubated at 37° C. At predetermined intervals (1 hour, 3 hours, 6 hours, 12 hours and 24 hours), NP treated biofilm was washed with 1×PBS. Following this, 30 µL SYPRO Ruby stain solution was added to each well and samples were incubated for up to 30 minutes at RT. The stained samples were rinsed gently with water to remove all excess stain and incubated in 200 µL of water for imaging. Samples were imaged using a confocal laser scanning microscope (CLSM, A1R confocal laser microscope, Nikon Instruments, Inc., Melville, NY) with an Apo LWD 25×/1.10 W water immersion objective.

The formation of extracellular polymeric substances (EPS) plays a vital role in the resistance of biofilm towards antimicrobial agents. The net negative charge of EPS can sequester positively charged antimicrobial agents or repel negatively charged antimicrobial agents. Accordingly, the penetration ability for antibiofilm active agent delivery systems was studied. The fluorescence spectra of gelatin, CS, HA, GNP, Doxy-GNP, CS-Doxy-GNP and HA-CS-Doxy-GNP with different concentrations were analyzed by a plate reader with excitation wavelength at 480 nm. The penetration of GNPs, CS-GNPs and HA-CSGNPs into *V. vulnificus* biofilm was monitored using CLSM (FIG. 8). Biofilm EPS was observed in red, through staining with FilmTracer SYPRO Ruby, while GNPs, CS-GNPs and HA-CS-GNPs were observed via auto-fluorescence. FIG. 9(*a*) depicts fluorescence spectra of blank GNPs, gelatin, CS, and HA with different concentrations. FIG. 9(*b*) depicts 100 µg/mL Doxy loaded NPs. The bonds of the Schiff base (C=N) and carbon double bonds (C=C) formed from the amine groups of gelatins and the glutaraldehyde crosslinker produce autofluorescence in each of the NP formulations. See B. Cai, L. Rao, X. Ji, L.-L. Bu, Z. He, D. Wan, Y. Yang, W. Liu, S. Guo and X.-Z. Zhao, *Journal of Biomedical Materials Research Part A,* 2016, 104, 2854-2860. Compared with GNPs and CS-GNPs, HA-CS-GNPs were able to penetrate and remain stable longer within pre-formed *V. vulnificus* biofilms.

Example IX

Effects of NPs on Planktonic Bacteria and Biofilm Formation In Vitro

The minimum inhibitory concentrations (MICs) of NPs against *V. vulnificus* were determined using the microdilution assay as previously reported. See T. Gwisai, N. R. Hollingsworth, S. Cowles, N. Tharmalingam, E. Mylonakis, B. B. Fuchs and A. Shukla, *Biomedical Materials,* 2017, 12, 045010; D. Alkekhia and A. Shukla, *Journal of Biomedical Materials Research Part A,* 2019, 107, 1324-1339. Free Doxy and Doxy loaded NPs were diluted 2-fold in LB in 96-well plates to obtain concentrations of Doxy or loaded Doxy ranging from 0.03-4.0 µg/mL. *V. vulnificus* in LB media in its logarithmic growth phase was added to each well at a final concentration of $1 \times 10^5$ colony forming units (CFU)/mL. Positive control (PC) of bacteria cultured in LB only and negative control (NC) of LB without bacteria were included. After 16-18 hours of shaking (100 rpm) at 37° C., $OD_{600}$ was measured using a plate reader. The normalized bacteria density (%) was calculated as follows:

$$\text{Normalized bacteria density (\%)} = \frac{OD600_{sample} - OD600_{NC}}{OD600_{PC} - OD600_{NC}} \times 100$$

The investigate the effect of free Doxy and Doxy-loaded NPs on *V. vulnificus* biofilm formation, *V. vulnificus* was prepared for biofilm formation. When adding the bacteria in its logarithmic growth phase to 96-well plates, free Doxy or Doxy-loaded NPs were added simultaneously at varying concentrations. Bacteria lacking Doxy treatment were included as a PC and LBS without bacteria was included as a NC. Following a 24-hour incubation in static conditions, the biofilm biomass was quantified using crystal violet staining. Briefly, the supernatant media was gently removed, and biofilms were washed three times with 1×PBS. Next biofilms were stained with 200 µL 0.1% (w/v) crystal violet in 1×PBS for 15 minutes, followed by three 1×PBS washes. The stain was eluted by incubation with 200 µL of 100% ethanol with shaking (100 rpm) for 2 min at RT. The absorbance at 570 nm ($OD_{570}$) was measured using a plate reader. Normalized biofilm biomass was calculated as follows:

$$\text{Normalized biofilm biomass \%} = \frac{OD570_{sample} - OD570_{NC}}{OD570_{PC} - OD570_{NC}} \times 100$$

Antibacterial effects of free Doxy and Doxy loaded NPs were investigated against planktonic *V. vulnificus* bacteria in a microdilution assay. In this technique, serial dilutions of the free Doxy and Doxy loaded NPs were made and incubated with *V. vulnificus.* The lowest drug concentration preventing bacteria growth was identified as the MIC. FIG. 10(*a*) showed normalized *V. vulnificus* density over a range of concentrations for free Doxy and Doxy loaded NPs. The MICs of free Doxy and Doxy loaded NPs against *V. vulnificus* were determined to be 0.5 µg/mL.

The formation of a biofilm has huge impact on antibiotic resistance and infection progression. See D. Davies, *Nature Reviews Drug Discovery,* 2003, 2, 114-122. Therefore, minimum biofilm inhibitory concentration (MBIC) of antibacterial agents was evaluated. $MBIC_{80}$ was determined as the minimal concentration of antimicrobial agents, which inhibit the formation of biofilm by 80% in comparison to control (without any antimicrobial agent). A crystal violet staining method was used to evaluate the biofilm biomass content. FIG. 10(*b*) depicts the inhibition efficiency of free Doxy and Doxy loaded NPs against biofilm. Less biofilm formed with the increase of the concentrations of free Doxy and Doxy-loaded NPs. The $MBIC_{80}$ of free Doxy, same amount of Doxy loaded NPs were about 16 µg/mL.

Example X

The Effects of NPs on Mature Biofilms

The effect of treatment with free Doxy, Doxy-GNP, CS-Doxy-GNP, and HA-CS-Doxy-GNP of 48 h aged *V. vulnificus* biofilms was assessed by examining biofilm morphology and quantifying biomass and cell viability. Morphology assessment via ESEM, LIVE/DEAD viability staining, colony enumeration and crystal violet staining were performed after incubation of the biofilms with the various treatment groups at a Doxy concentration of 50 µg/mL in 1×PBS or with a 1×PBS control for 24 hours at 37° C.

Crystal Violet Assay

Biofilm biomass was assessed for 48 h mature biofilms formed in 96-well plates. These were gently washed with 1×PBS, and then incubated with serial dilutions of the various treatment groups at Doxy concentrations ranging from 0.78 to 50 µg/mL for 24 h. PCs of biofilms cultured in LBS at pH 5.5 and NCs of LBS at pH 5.5 without bacteria were included. Following 24 hours of incubation, the biofilm biomass was quantified using crystal violet staining as described earlier.

Morphology of *V. vulnificus* Biofilms

To assess morphology, biofilms were formed on the silicon wafer surface (0.5 cm×0.5 cm) placed in 24-well plates. After treatment, the biofilms were gently washed three times in 1×PBS and fixed with 2.5% (w/v) glutaraldehyde at 4° C. for 4 hours. After the biofilms were washed with 1×PBS, samples were dehydrated gradually through a series of ethanol concentrations of 50%, 60%, 70%, 90% and 100% (v/v) (10 minutes each). The dehydrated biofilms were lyophilized, sputter coated with goldpalladium, and imaged via ESEM as described for NP characterization.

LIVE/DEAD Bacterial Staining

For LIVE/DEAD viability staining, biofilms were formed on 8-well chambered cover glass. After treatment, staining was conducted according to the manufacturer protocol. Briefly, a working fluorescent stain solution was prepared by adding 3 µL of SYTO 9 stain and 3 µL of propidium iodide stain to 1 mL of water. Treated biofilms were incubated with 200 µL of this working solution for 30 minutes at RT, followed by rinsing three times with water to remove excess stain. The stained bacteria were imaged with CLSM with an Apo LWD 25×/1.10 W water immersion objective.

Colony Counting Assay

Colony enumeration was also conducted by first dispersing biofilms formed in 48-well plates by sonication following treatment. Each sample was then serially diluted in LB, and 10 mL of the dilution was plated onto LB agar plates. Agar plates were imaged and CFU were counted following incubation for 24 h at 37° C.

The eradication property of NPs against *V. vulnificus* biofilm were first evaluated through the minimal biofilm eradication concentration (MBEC) via crystal violet staining assay. $MBEC_{90}$ was defined as the concentration of antibacterial agents that reduced the biofilm initial biomass by 90% after treatment. The $MBEC_{90}$ of Doxy, Doxy-GNPs, CS-Doxy-GNPs and HA-CS-Doxy-GNPs were about 50 µg/mL (FIG. 11(*a*)). The morphology of the biofilm after treatment with PBS, free Doxy and Doxy loaded NPs was observed using SEM. As shown in FIG. 12(*a*), compared with the PBS treated biofilm, the biofilm exhibited an amount of removal after the treatment of free Doxy and Doxy loaded NPs. Most notably, significantly less biofilm remained after being treated with HA-CS-Doxy-GNPs indicating that treatment with HA-CS-Doxy-GNPs eliminated *V. vulnificus* biofilm.

The bacteria viability in biofilm was evaluated using a LIVE/DEAD staining based on SYTO 9 and propidium iodide. Green-fluorescent SYTO 9 permeates all bacterial membranes, whereas red-fluorescent propidium iodide only enters damaged bacterial membranes. The images from HA-CS-Doxy-GNP treated biofilm clearly show abundant green fluorescence labeled live bacteria in the PBS group. The yellow color is due to overlap of green and red color. As shown in FIG. 12(b), greater red fluorescence signals were observed after treatment with HA-CS-Doxy-GNPs, demonstrating more bacterial membrane damage induced by HA-CS-Doxy-GNPs.

To further quantify the viable bacteria in biofilms, CFU was also enumerated after treatment with each GNP and free Doxy (FIGS. 11(b) and 11(c)), showing a large reduction in CFU (2 log reduction) with therapeutic treatment compared to a no treatment control, with the least colonies observed visually with the HA-CS-Doxy-GNPs. See FIG. 11(b) which are photographs of bacterial colonies formed of V. vulnificus biofilm after being treated with PBS, 50 µg/mL Doxy and Doxy loaded NPs (50 µg/mL Doxy) for 24 hours.

Example XI

Ex Vivo Pig Skin Infection Model

Frozen porcine skin tissue was thawed and washed with 1×PBS. A biopsy punch (8 mm) was used to create tissue sections from freshly thawed tissue. A 1.5-mm deep well was created in the center of each of these skin samples using a smaller 3-mm biopsy punch. The tissue pieces were sterilized by immersing in 70% (v/v) ethanol for 2 hours and drying for 30 minutes in a CellGard™ Energy Saver class II, type A2 biosafety cabinet (NuAire, Plymouth, MN). The sterile tissue was then placed on soft TSB agar plates containing 0.5% (w/v) agar with 100 µg/mL vancomycin. Note that vancomycin was included as a common antibiotic against gram-positive to prevent contamination by non-V. vulnificus bacteria. The skin was then infected by adding 10 µL of V. vulnificus suspension (OD$_{600}$=0.1) in the 3 mm diameter well in each sample. The inoculated skin pieces were incubated for 48 hours at 37° C. in a humidified chamber. The tissue samples were transferred to a new agar plate every 24 hours. At 48 hours, 15 µL of Doxy or HA-CS-Doxy-GNP at a Doxy concetration of 10, 50 or 100 µg/mL was added to the infected skin samples and incubated for a further 24 hours. Controls of tissue inoculated with bacteria treated with LBS at pH 5.5 only and tissue without bacteria treated with LBS at pH 5.5 were included as controls. After incubation, skin samples were washed with sterile 1×PBS and homogenized by using a gentleMACS™ dissociator (Miltenyi Biotec, Waltham, MA). The homogenized samples were serially diluted 10-fold ($10^1$ to $10^6$) and each dilution plated onto LB agar plates. The plates were incubated at 37° C. for 24 hours followed by CFU enumeration.

The ex vivo pig skin model used to evaluate the antimicrobial efficacy of the NPs against V. vulnificus is shown in FIG. 13(a), FIG. 13(b) and FIG. 13(c) showed the antibacterial effectiveness of the formulations against V. vulnificus when grown for 2 days on pig skin ex vivo and then treated with the NPs for 24 hours. Compared with the untreated pig skin samples, Doxy and HA-CS-Doxy-GNP containing 50 µg/mL or 100 µg/mL Doxy significantly reduced the number of living bacterial cells as shown in FIG. 13(b). With the increase of free Doxy or Doxy loaded NPs, the CFU/mL reduced. After treating with HA-CS-Doxy-GNP containing 100 mg/mL or free Doxy, the mean value of CFU/mL was reduced from 100% for untreated samples to 16.42% for Doxy and 8.29% for HA-CS-Doxy-GNP. Thus, the HA-CS-Doxy-GNPs were demonstrated to efficiently eradicate V. Vulnificus on pig skin ex vivo at high concentrations of loaded drug.

Example XII

Biocompatibility In Vitro
CCK-8 Assay

The cytotoxicity of each NP formulation was evaluated for HUVEC and NIH-13T3 using a CCK-8 viability assay. Briefly, HUVEC and NIH 3T3 cells were cultured at a density of ~5000 cells/cm$^2$ in EGM-2 endothelial cell growth medium and DMEM supplemented with 10% (v/v) FBS and 1% (v/v) penicillin/streptomycin, respectively at 37° C. with 5% CO$_2$. After 24 hours, cells were treated with Doxy, Doxy-GNPs, CS-Doxy-GNP and HA-CS-Doxy-GNP at a Doxy concentration of 50 µg/mL in the respective media. Cells treated with media only and wells containing no cells or NPs were included as PCs and NCs, respectively. Following a 24 hour incubation, the media was removed, cells were rinsed with 1×PBS three times and 10 µL of CCK-8 solutions was added to each well. After incubation for 4 hours at 37° C. with 5% CO$_2$, the absorbance was read at 450 nm (OD$_{450}$) using a plate reader. Normalized cell viability was calculated using the following equation.

$$\text{Cell viability (\%)} = \frac{OD450_{sample} - OD450_{NC}}{OD450_{PC} - OD450_{NC}} \times 100$$

To assess the toxicity of NPs towards cells in furtherance of therapeutic treatment, toxicity profiles of Doxy and Doxy loaded NPs with 50 µg/mL Doxy on HUVEC and NIH 3T3 cells were determined CCK-8 assay. FIG. 14 showed that the cell viability of all Doxy loaded NPs was about 80% when loading with 50 µg/mL Doxy. However, cell viability of NIH 3T3 cells to free Doxy was about 70% cell viability of HUVEC cells to free Doxy was about 60%. These findings demonstrated that the Doxy loaded NPs displayed lower cytotoxicity to both HUVEC and NIH 3T3 cells compared to free Doxy.
Hemolysis Assay RBC hemolysis was assessed as previously reported (see N. Vera-Gonzalez, C. M. Bailey-Hytholt, L. Langlois, F. de Camargo Ribeiro, E. L. de Souza Santos, J. C. Junqueira and A. Shukla, Journal of Biomedical Materials Research Part A, 2020, 108, 2263-2276; H. Liu, S. Shukla, N. Vera-Gonzalez, N. Tharmalingam, E. Mylonakis, B. B. Fuchs and A. Shukla, Frontiers in Cellular and Infection Microbiology, 2019, 9, 37) by incubating 100 µL of free Doxy and Doxy-GNPs, CS-Doxy-GNPs, or HA-CS-Doxy-GNPs at a Doxy concentrations of 1.56 to 200 µg/mL with 100 µL 5% BRBCs or HRBCs in 96-well plates at 37° C. for 2 h. Blank NPs at concentrations ranging from 31.25 to 4000 µg/mL were also tested, along with 0.1% (v/v) Triton X-100 and 1×PBS and PCs and NCs, respectively. After incubation, the plates were centrifuged at 1000 rpm for 5 minutes. A 100 µL aliquot of the supernatant from each well was transferred to a 96-well plate. The absorbance of the supernatant was measured at 540 nm (OD$_{540}$). The hemolysis ratio was calculated using the following equation.

$$\text{Hemolysis (\%)} = \frac{OD570_{sample} - OD570_{NC}}{OD570_{PC} - OD570_{NC}} \times 100$$

Figures 15A, 15B, 15C, 15D:
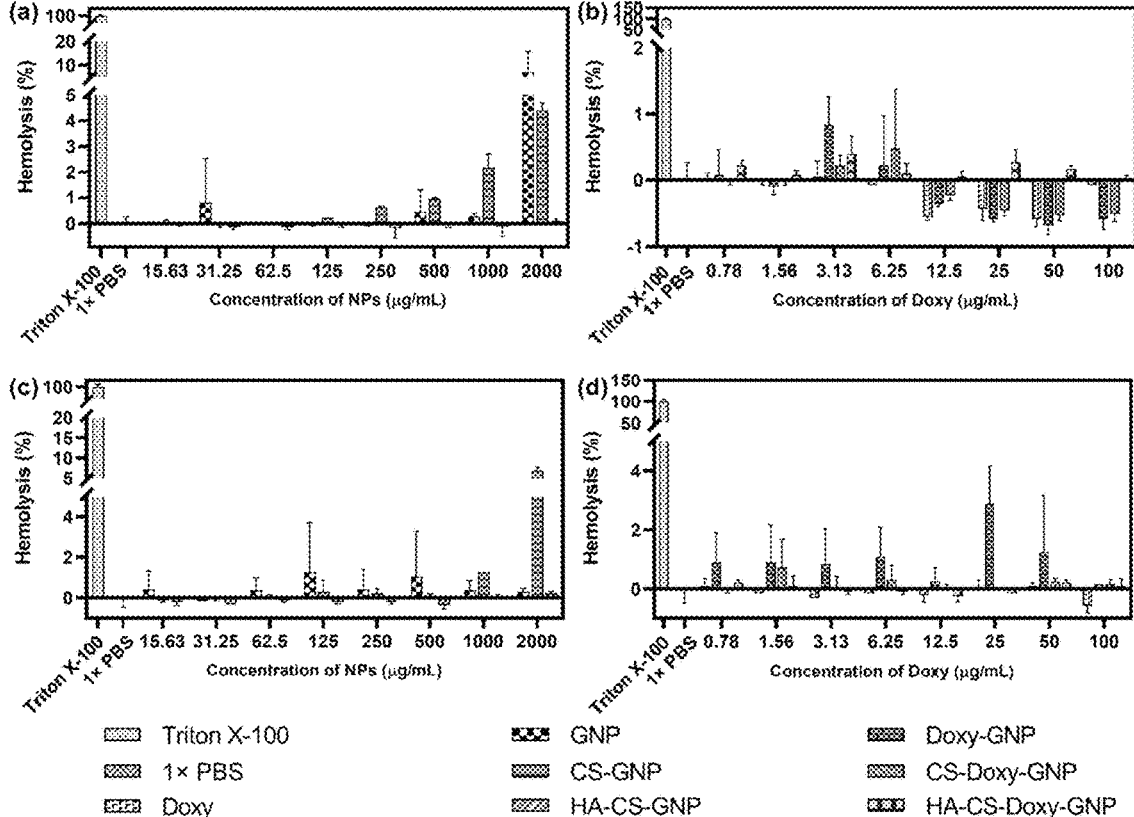

The hemolysis of blank NPs (15.63, 31.25, 62.5, 125, 250, 500, 1000, 2000 µg/mL), Doxy (0.78, 1.56, 3.13, 6.25, 12.5, 25, 50, 100 µg/mL) and Doxy loaded NPs (containing 0.78, 1.56, 3.13, 6.25, 12.5, 25, 50, 100 µg/mL of Doxy) (final concentrations) was investigated. FIGS. 15(a) and 15(b) depict normalized hemolysis of BRBCs exposed to blank NPs and Doxy loaded NPs. FIGS. 15(a) and 15(b) depict normalized hemolysis of HRBCs exposed to blank NPs and Doxy loaded NPs at different concentrations. Statistical significance (****p<0.0001) between time points is indicated using two-way ANOVA with Tukey's post hoc analysis.

As shown in FIGS. 15(b) and 15(d), even though the concentrations increased to the maximum, the hemolysis ratios were lower than 5%, which was considered good hemocompatibility. And the percent hemolysis of BRBCs and HRBCs observed was extremely low (<0.5%) for the HA-CS-Doxy-GNPs even at concentrations above the MBEC$_{90}$, indicating excellent hemocompatibility of these NPs. Therefore, the nanoparticles as described herein exhibited extremely low toxicity.

Example XIII

Statistical Analysis

Data were presented as the mean±standard deviation (SD) of three biological replicates at minimum. Statistical analysis was performed with GraphPad Prism using either one- or two-way analysis of variance (ANOVA; α=0.05) with Tukey's post-hoc analysis. Statistical significance was represented as follows, *p<0.05, p<0.01, *p<0.001, ****p<0.0001.

Example XIV

Embodiments

Embodiments of the present disclosure are directed to a method of delivering an antibiotic to bacteria within a biofilm. The method includes contacting the biofilm with a nanoparticle including (1) a core comprising gelatin and an antibiotic, (2) at least one layer surrounding the core, wherein the at least one layer is responsive to a first condition of the biofilm thereby allowing access to the core of a second condition of the biofilm, wherein the core is responsive to the second condition of the biofilm, and wherein the at least one layer responds to the first condition of the biofilm to expose the core which is then responsive to the condition of the biofilm to release the antibiotic, and wherein the antibiotic is delivered to the bacteria. According to one aspect the first condition is an enzyme produced by the bacteria and the at least one layer is degraded. According to one aspect, the first condition is pH and the at least one layer swells in response to the pH. According to one aspect, the second condition is an enzyme produced by the bacteria and the core is degraded. According to one aspect, the nanoparticle includes at least two layers surrounding the core. According to one aspect, the nanoparticle includes a first layer contacting the core, wherein the first layer includes chitosan. According to one aspect, the nanoparticle includes an outer layer, wherein the outer layer includes hyaluronic acid. According to one aspect, the nanoparticle includes an inner first layer including chitosan and an outer layer including hyaluronic acid. According to one aspect, the nanoparticle includes an inner first layer including chitosan contacting the core and an outer layer contacting the inner layer and including hyaluronic acid. According to one aspect, the nanoparticle includes an inner first layer including chitosan contacting the core and an outer layer contacting the inner layer and including hyaluronic acid, wherein the hyaluronic acid is responsive to hyaluronidase which degrades the hyaluronic acid, wherein the chitosan is responsive to pH which swells the chitosan, and wherein the core is responsive to gelatinase which degrades the gelatin of the core.

Embodiments of the present disclosure include a nanoparticle including a core including gelatin and an antibiotic, an inner layer including chitosan surrounding the core, and an outer layer including hyaluronic acid surrounding the inner layer.

Embodiments of the present disclosure include a nanoparticle including a core, an inner layer and an outer layer, wherein an antibiotic is present in the core or the inner layer, and optionally conjugated or covalently linked or bound to the core or inner layer material. According to one aspect, the core includes gelatin and the antibiotic. According to one aspect, the inner layer includes gelatin and the antibiotic.

Embodiments of the present disclosure include a nanoparticle including a core, and a plurality of layers surrounding the core, wherein an antibiotic is present in one or more of the core and one or more layers of the plurality of layers, and optionally conjugated or covalently linked or bound to the core or inner layer material.

Embodiments of the present disclosure include a pharmaceutical composition including a nanoparticle including a core including gelatin and an antibiotic, an inner layer including chitosan surrounding the core, and an outer layer including hyaluronic acid surrounding the inner layer, and a pharmaceutically acceptable excipient.

Embodiments of the present disclosure include a pharmaceutical composition including a nanoparticle including a core, an inner layer and an outer layer, wherein an antibiotic is present in the core or the inner layer, and optionally conjugated or covalently linked or bound to the core or inner layer material, and a pharmaceutically acceptable excipient.

Embodiments of the present disclosure include a pharmaceutical composition including a nanoparticle including a core, and a plurality of layers surrounding the core, wherein an antibiotic is present in one or more of the core and one or more layers of the plurality of layers, and optionally conjugated or covalently linked or bound to the core or inner layer material, and a pharmaceutically acceptable excipient.

Embodiments of the present disclosure are directed to a method of treating a subject in need thereof for a bacterial infection including the step of administering to the subject a nanoparticle including a core including gelatin and an antibiotic, an inner layer including chitosan surrounding the core, and an outer layer including hyaluronic acid surrounding the inner layer, wherein the bacterial infection is prevented, reduced, inhibited or eradicated. According to one aspect, the nanoparticle is administered by systemic administration or topical administration. According to one aspect, the subject is a mammal. According to one aspect, the subject is a human.

Embodiments of the present disclosure are directed to a method of treating a subject in need thereof for a bacterial infection including the step of administering to the subject a nanoparticle including a core, an inner layer and an outer layer, wherein an antibiotic is present in the core or the inner layer, and optionally conjugated or covalently linked or bound to the core or inner layer material, wherein the bacterial infection is prevented, reduced, inhibited or eradicated. According to one aspect, the nanoparticle is administered by systemic administration or topical administration. According to one aspect, the subject is a mammal. According to one aspect, the subject is a human.

Embodiments of the present disclosure are directed to a method of treating a subject in need thereof for a bacterial infection including the step of administering to the subject a nanoparticle including a core, and a plurality of layers surrounding the core, wherein an antibiotic is present in one or more of the core and one or more layers of the plurality of layers, and optionally conjugated or covalently linked or bound to the core or inner layer material, wherein the bacterial infection is prevented, reduced, inhibited or eradicated. According to one aspect, the nanoparticle is administered by systemic administration or topical administration. According to one aspect, the subject is a mammal. According to one aspect, the subject is a human.

Embodiments of the present disclosure are directed to a method of making a nanoparticle including providing a gelatin core including an antibiotic with a layer of chitosan, and providing a layer of hyaluronic acid over the layer of chitosan.

The invention claimed is:

1. A method of treating a bacterial infection within a subject in need thereof, wherein the bacterial infection is characterized by a bacterial biofilm comprising
   administering to the subject a nanoparticle comprising
      (1) a core comprising gelatin and an antibiotic,
      (2) an inner first layer comprising chitosan surrounding the core and
      (3) an outer layer comprising hyaluronic acid surrounding the inner first layer at least one layer surrounding the core,
   wherein, after administration, the nanoparticle contacts the bacterial biofilm,
   wherein the hyaluronic acid is responsive to hyaluronidase in the bacterial biofilm which degrades the hyaluronic acid to expose the chitosan,
   wherein the chitosan is responsive to the pH of the bacterial biofilm, which swells the chitosan thereby allowing gelatinase in the bacterial biofilm to contact the gelatin, and
   wherein gelatinase in the bacterial biofilm degrades the gelatin of the core to release the antibiotic, to kill the bacteria.

2. The method of claim 1 wherein the bacterial infection is reduced, inhibited or eradicated.

3. The method of claim 1 wherein the nanoparticle is within a pharmaceutical composition comprising a pharmaceutically acceptable excipient.

4. A method of delivering an antibacterial to a bacterial infection within a subject in need thereof, wherein the bacterial infection is characterized by a bacterial biofilm comprising

30 administering to the subject a pharmaceutical composition comprising a nanoparticle in a pharmaceutically acceptable carrier, wherein the nanoparticle comprises
      (1) a core comprising gelatin and an antibacterial,
      (2) an inner first layer comprising chitosan surrounding the core and
      (3) an outer layer comprising hyaluronic acid surrounding the inner first layer at least one layer surrounding the core,
   wherein, after administration, the nanoparticle contacts the bacterial biofilm,
   wherein the hyaluronic acid is responsive to hyaluronidase in the bacterial biofilm which degrades the hyaluronic acid to reveal the chitosan,
   wherein the chitosan is responsive to the pH of the bacterial biofilm which swells the chitosan thereby allowing gelatinase in the bacterial biofilm to contact the gelatin, and
   wherein gelatinase in the bacterial biofilm degrades the gelatin of the core to release the antibacterial, such that the antibacterial contacts bacteria within the bacterial biofilm.

5. The method of claim 4 wherein the bacterial infection is reduced, inhibited or eradicated.

6. A method of treating a bacterial biofilm within an individual in need thereof comprising
   administering to the subject a nanoparticle comprising
      (1) a core comprising gelatin and an antibiotic
      (2) an inner first layer comprising chitosan surrounding the core, and
      (3) an outer layer comprising hyaluronic acid surrounding the inner layer
   wherein, after administration, the nanoparticle contacts the bacterial biofilm,
   wherein the hyaluronic acid is responsive to hyaluronidase in the bacterial biofilm which degrades the hyaluronic acid revealing the inner first layer comprising chitosan,
   wherein the chitosan is responsive to the pH of the bacterial biofilm which swells the chitosan thereby allowing gelatinase in the bacterial biofilm to contact the gelatin, and
   wherein the gelatinase in the bacterial biofilm degrades the gelatin of the core to release the antibiotic, thereby treating the bacterial biofilm.

7. The method of claim 6 wherein the nanoparticle is within a pharmaceutical composition comprising a pharmaceutically acceptable excipient.

* * * * *